United States Patent
Kapur et al.

(10) Patent No.: US 12,220,704 B2
(45) Date of Patent: Feb. 11, 2025

(54) CONCENTRATING PARTICLES IN A MICROFLUIDIC DEVICE

(71) Applicant: The General Hospital Corporation, Boston, MA (US)

(72) Inventors: Ravi Kapur, Sharon, MA (US); Kyle C. Smith, Cambridge, MA (US); Mehmet Toner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 18/595,927

(22) Filed: Mar. 5, 2024

(65) Prior Publication Data

US 2024/0198339 A1    Jun. 20, 2024

Related U.S. Application Data

(60) Continuation of application No. 17/335,510, filed on Jun. 1, 2021, now Pat. No. 11,944,972, which is a
(Continued)

(51) Int. Cl.
*B01L 3/00* (2006.01)
*A61K 35/28* (2015.01)
(Continued)

(52) U.S. Cl.
CPC ........ *B01L 3/502761* (2013.01); *A61K 35/28* (2013.01); *B01L 3/502715* (2013.01);
(Continued)

(58) Field of Classification Search
CPC ......... B01L 3/502761; B01L 3/502715; B01L 3/502746; B01L 3/502753;
(Continued)

(56) References Cited

U.S. PATENT DOCUMENTS 5,968,820 A    10/1999   Zborowski et al.
6,540,896 B1    4/2003   Manz et al.
(Continued)

FOREIGN PATENT DOCUMENTS

CN    101678356    3/2010
CN    101765762 A  6/2010
(Continued)

OTHER PUBLICATIONS

Augustsson et al., "Microfluidic, Label-Free Enrichment of Prostate Cancer Cells in Blood Based on Acoustophoresis," Anal. Chem., 84(18):7954-7965, Sep. 2012.
(Continued)

*Primary Examiner* — Brian J. Sines
(74) *Attorney, Agent, or Firm* — Fish & Richardson P.C.

(57) ABSTRACT

A microfluidic device includes: a first microfluidic channel; a second microfluidic channel extending along the first microfluidic channel; and a first array of islands separating the first microfluidic channel from the second microfluidic channel, in which each island is separated from an adjacent island in the array by an opening that fluidly couples the first microfluidic channel to the second microfluidic channel, in which the first microfluidic channel, the second microfluidic channel, and the islands are arranged so that a fluidic resistance of the first microfluidic channel increases relative to a fluidic resistance of the second microfluidic channel along a longitudinal direction of the first microfluidic channel such that, during use of the microfluidic device, a portion of a fluid sample flowing through the first microfluidic channel passes through one or more of the openings between adjacent islands into the second microfluidic channel.

25 Claims, 16 Drawing Sheets

Related U.S. Application Data continuation of application No. 16/211,362, filed on Dec. 6, 2018, now Pat. No. 11,052,393, which is a division of application No. 14/931,421, filed on Nov. 3, 2015, now Pat. No. 10,150,116.

(60) Provisional application No. 62/074,213, filed on Nov. 3, 2014, provisional application No. 62/074,315, filed on Nov. 3, 2014.

(51) Int. Cl.
| | |
|---|---|
| G01N 1/40 | (2006.01) |
| G01N 15/00 | (2024.01) |
| G01N 15/01 | (2024.01) |
| G01N 15/02 | (2024.01) |
| G01N 15/06 | (2024.01) |
| G01N 15/14 | (2024.01) |
| G01N 15/149 | (2024.01) |

(52) U.S. Cl.
CPC ... *B01L 3/502746* (2013.01); *B01L 3/502753* (2013.01); *G01N 1/4077* (2013.01); *G01N 15/0255* (2013.01); *G01N 15/0618* (2013.01); *G01N 15/1484* (2013.01); *B01L 3/502776* (2013.01); *B01L 2200/0631* (2013.01); *B01L 2200/0647* (2013.01); *B01L 2200/0652* (2013.01); *B01L 2200/0668* (2013.01); *B01L 2200/0684* (2013.01); *B01L 2200/12* (2013.01); *B01L 2300/0681* (2013.01); *B01L 2300/0877* (2013.01); *B01L 2300/185* (2013.01); *B01L 2400/0409* (2013.01); *B01L 2400/0415* (2013.01); *B01L 2400/043* (2013.01); *B01L 2400/0436* (2013.01); *B01L 2400/0457* (2013.01); *B01L 2400/0487* (2013.01); *B01L 2400/082* (2013.01); *G01N 2001/4088* (2013.01); *G01N 2015/0053* (2013.01); *G01N 15/01* (2024.01); *G01N 2015/0288* (2013.01); *G01N 2015/1486* (2013.01); *G01N 15/149* (2024.01); *G01N 2015/1493* (2013.01)

(58) Field of Classification Search
CPC ..... B01L 2200/0652; B01L 2200/0647; B01L 3/502776; B01L 2200/0631; B01L 2200/0668; B01L 2200/0684; B01L 2200/12; B01L 2300/0681; B01L 2300/0877; B01L 2300/185; B01L 2400/0409; B01L 2400/0415; B01L 2400/043; B01L 2400/0436; B01L 2400/04571; B01L 2400/082; A61K 35/28; G01N 1/4077; G01N 15/0255; G01N 15/0618; G01N 15/1484; G01N 15/149; G01N 15/01; G01N 2001/4088; G01N 2015/0053; G01N 2015/0288; G01N 2015/1486; G01N 2015/1493
See application file for complete search history.

(56) References Cited

U.S. PATENT DOCUMENTS

| | | |
|---|---|---|
| 6,632,652 B1 | 10/2003 | Austin et al. |
| 6,767,706 B2 | 7/2004 | Quake et al. |
| 7,560,267 B2 | 7/2009 | Yang et al. |
| 7,641,865 B2 | 1/2010 | Tonkovich et al. |
| 7,837,040 B2 | 11/2010 | Ward et al. |
| 8,021,614 B2 | 9/2011 | Huang et al. |
| 8,186,913 B2 | 5/2012 | Toner et al. |
| 8,906,322 B2 | 12/2014 | Huang et al. |
| 10,150,116 B2 * | 12/2018 | Kapur ............... G01N 15/0618 |
| 11,052,393 B2 * | 7/2021 | Kapur ............... B01L 3/502761 |
| 11,944,972 B2 * | 4/2024 | Kapur ............... B01L 3/502746 |
| 2002/0187503 A1 | 12/2002 | Harrold et al. |
| 2003/0092029 A1 | 5/2003 | Josephson et al. |
| 2003/0124194 A1 | 7/2003 | Gaw et al. |
| 2003/0175944 A1 | 9/2003 | Yang et al. |
| 2003/0226806 A1 | 12/2003 | Young et al. |
| 2004/0033515 A1 | 2/2004 | Cao et al. |
| 2004/0053403 A1 | 3/2004 | Jedrzejewski et al. |
| 2004/0126890 A1 | 7/2004 | Gjerde et al. |
| 2004/0144651 A1 | 7/2004 | Huang et al. |
| 2005/0109716 A1 | 5/2005 | Leach et al. |
| 2006/0068490 A1 | 3/2006 | Tang et al. |
| 2006/0078888 A1 | 4/2006 | Griffiths et al. |
| 2006/0160243 A1 | 7/2006 | Tang et al. |
| 2006/0269965 A1 | 11/2006 | Josephson et al. |
| 2007/0026381 A1 | 2/2007 | Huang et al. |
| 2007/0026419 A1 | 2/2007 | Fuchs et al. |
| 2007/0059781 A1 | 3/2007 | Kapur et al. |
| 2007/0099207 A1 | 5/2007 | Fuchs et al. |
| 2007/0196820 A1 | 8/2007 | Kapur et al. |
| 2008/0023399 A1 | 1/2008 | Inglis et al. |
| 2009/0032449 A1 | 2/2009 | Mueth et al. |
| 2009/0269767 A1 | 10/2009 | Soderlund et al. |
| 2010/0006479 A1 | 1/2010 | Reichenbach |
| 2010/0059414 A1 | 3/2010 | Sturm et al. |
| 2011/0091987 A1 | 4/2011 | Weissleder et al. |
| 2012/0037544 A1 | 2/2012 | Lane et al. |
| 2012/0258459 A1 | 10/2012 | Huang |
| 2013/0079251 A1 | 3/2013 | Boles |
| 2013/0086980 A1 | 4/2013 | Gadini et al. |
| 2013/0121895 A1 | 5/2013 | Tang et al. |
| 2013/0168298 A1 | 7/2013 | Huang et al. |
| 2013/0228530 A1 | 9/2013 | Di Carlo et al. |
| 2014/0030788 A1 | 1/2014 | Chen et al. |
| 2014/0093867 A1 | 4/2014 | Burke et al. |
| 2014/0227777 A1 | 8/2014 | Choi et al. |
| 2014/0248621 A1 | 9/2014 | Collins |
| 2014/0342375 A1 | 11/2014 | Grisham et al. |
| 2015/0202356 A1 | 7/2015 | Gifford |
| 2016/0047735 A1 | 2/2016 | Grisham et al. |
| 2016/0139012 A1 | 5/2016 | D'Silva et al. |
| 2016/0363523 A1 | 12/2016 | Reichenbach |
| 2017/0209864 A1 | 7/2017 | Grisham et al. |
| 2017/0225166 A1 | 8/2017 | Toner et al. |
| 2017/0254774 A1 | 9/2017 | Sabin et al. |
| 2020/0139370 A1 | 5/2020 | Kapur et al. |
| 2020/0353470 A1 | 11/2020 | Hoonejani et al. |
| 2021/0252514 A1 | 8/2021 | Kapur et al. |

FOREIGN PATENT DOCUMENTS

| | | |
|---|---|---|
| CN | 102791616 A | 11/2012 |
| JP | 2004-170396 | 6/2004 |
| JP | 2007-196219 | 8/2007 |
| JP | 2013-515599 | 5/2013 |
| WO | WO 2000/061191 | 10/2000 |
| WO | WO 2004/037374 | 5/2004 |
| WO | WO 2004/074814 | 9/2004 |
| WO | WO 2005/086703 | 9/2005 |
| WO | WO 2006/108087 | 10/2006 |
| WO | WO 2010/123594 | 10/2010 |
| WO | WO 2011/132164 | 10/2011 |
| WO | WO 2012/067985 | 5/2012 |
| WO | WO 2014/004577 | 1/2014 |
| WO | WO 2014/107240 | 7/2014 |
| WO | WO 2015/116990 | 8/2015 |

OTHER PUBLICATIONS

Burke et al., "High-throughput particle separation and concentration using spiral inertial filtration," Biomicrofluidics 8, 024105 (2014), 18 pages.
CN Office Action in Chinese Appln. No. 201580069630.7 dated Mar. 19, 2020, 18 pages (with English translation).
CN Office Action in Chinese Appln. No. 201580069630.7, dated Apr. 2, 2019, 23 pages (with English translation).

(56) References Cited

OTHER PUBLICATIONS

CN Office Action in Chinese Appln. No. 201580071263.4, dated Apr. 2, 2019, 34 pages (with English translation).
CN Office Action in Chinese Appln. No. 201580071263.4, dated Mar. 9, 2020, 8 pages (with English translation).
CN Office Action in Chinese Appln. No. 201580071415.0, dated Apr. 2, 2019, 26 pages (with English translation).
CN Office Action in Chinese Appln. No. 201580071415.0, dated Mar. 19, 2020, 16 pages (with English translation).
D'Avino et al., "Single line particle focusing induced by viscoelasticity of the suspending liquid: theory, experiments and simulations to design a micropipe flow-focuser," Lab Chip, 12(9):1638-1645, Feb. 2012.
Del Giudice et al., "Particle alignment in a viscoelastic liquid flowing in a square-shaped microchannel," Lab Chip, 2013, 13, pp. 4263-4271, Aug. 2013.
Di Carlo et al., "Continuous inertial focusing, ordering, and separation of particles in microchannels," Proc. Natl. Acad. Sci. U.S.A., 104(48):18892-18897, Nov. 2007.
Di Carlo et al., "Particle segregation and dynamics in confined flows," Phys. Rev. Lett., 102(9):094503, Mar. 2009.
Di Carlo, "Inertial microfluidics," Lab Chip, 9(21):3038-3046, Aug. 2009.
EP Extended European Search Report in European Appln. No. 15856423.7, dated Apr. 20, 2018, 8 pages.
EP Extended European Search Report in European Appln. No. 15856708.1, dated May 16, 2018, 9 pages.
EP Extended European Search Report in European Appln. No. 15856773.5, dated Apr. 20, 2018, 9 pages.
EP Extended European Search Report in European Appln. No. 20176266, dated Aug. 28, 2020, 11 pages.
EP Extended European Search Report in European Appln. No. 21152033.3, dated Jul. 8, 2021, 8 pages.
EP Office Action in European Appln. No. 15,856,773, dated Jun. 24, 2020, 4 pages.
EP Office Action in European Appln. No. 15856708.1, dated Dec. 3, 2019, 6 pages.
EP Office Action in European Appln. No. 15856773.5, dated Dec. 2, 2019, 6 pages.
Gifford et al., "Controlled Incremental Filtration: A simplified approach to design and fabrication of high-throughput microfluidic devices for selective enrichment of particles," Lab Chip, DOI: 10.1039/C4LC00785A, Sep. 2014, 30 pages.
IN Office Action in Indian Appln. No. 201737016632, dated Mar. 2, 2020, 8 pages.
IN Office Action in Indian Appln. No. 201737018681, dated Aug. 29, 2020, 8 pages.
IN Office Action in Indian Appln. No. 201737018682, dated May 22, 2019, 6 pages.
Inglis, "Efficient Microfluidic Particle Separation Arrays," American Institute of Physics, Jan. 9, 2009, 013510-1 to 013510-3.
JP Office Action in Japanese Appln. No. 2017-523989, dated Jan. 7, 2020, 9 pages (with English translation).
JP Office Action in Japanese Appln. No. 2017-523990, dated Dec. 18, 2018, 10 pages (with English translation).
JP Office Action in Japanese Appln. No. 2017-523990, dated Jun. 7, 2019, 7 pages (with English translation).
Kang et al., "DNA-based highly tunable particle focuser," Nature Communications, 4:2567, Oct. 2013, 8 pages.
Lee et al., "Dynamic self-assembly and control of microfluidic particle crystals," Proceedings of the National Academy of Sciences, 107(52):22413-22418, Nov. 2010.
Lee et al., "Multiplex Particle Focusing via Hydrodynamic Force in Viscoelastic Fluids," Scientific Reports, 3:3258, Nov. 2013, 8 pages.
Lim et al., "Inertio-elastic focusing of bioparticles in microchannels at high throughput," Nature Communications, (5:4120), pp. 1-9, Jun. 2014.
Loutherback, "Microfluidic Devised for High Throughput Cell Sorting and Chemical Treatment," Dissertation, Nov. 2011.
Lubbersen et al., "High throughput particle separation with a mirrored deterministic ratchet design", Chemical Engineering and Processing 77 (2014) 42-49.
Lubbersen et al., "Visualization of inertial flow in deterministic ratchets", Separation and Purification Technology 109 (2013) 33-39.
Martel and Toner, "Inertial Focusing in Microfluidics," Annual Review of Biomedical Engineering, 16:371-396, Jul. 2014.
Martel and Toner, "Particle Focusing in Curved Microfluidic Channels," Scientific Reports, 3(3340): 1-8, Nov. 2013.
Notice of Allowance in Japanese Appln. No. 2020-005143, dated Dec. 28, 2021, 5 pages (with English translation).
Office Action in Canadian Appln. No. 2,966,603, dated Nov. 5, 2021, 3 pages.
Office Action in Canadian Appln. No. 2,966,611, dated Feb. 22, 2023, 3 pages.
Office Action in Canadian Appln. No. 2,966,611, dated Nov. 5, 2021, 3 pages.
Office Action in Canadian Appln. No. 2,966,611, dated Sep. 8, 2022, 3 pages.
Office Action in Canadian Appln. No. 2,966,623, dated Feb. 21, 2023, 3 pages.
Office Action in Canadian Appln. No. 2,966,623, dated Nov. 12, 2021, 3 pages.
Office Action in Canadian Appln. No. 2,966,623, dated Sep. 9, 2022, 5 pages.
Office Action in U.S. Appl. No. 14/931,223, dated May 19, 2017, 15 pages.
Office Action in U.S. Appl. No. 14/931,421, dated May 19, 2017, 19 pages.
Office Action in U.S. Appl. No. 14/931,421, dated Oct. 4, 2017, 15 pages.
PCT International Preliminary Report on Patentability in International Appln. No. PCT/US2015/058841, dated May 9, 2017, 16 pages.
PCT International Search Report and Written Opinion in International Appln. No. PCT/US2015/058785, dated Feb. 16, 2016, 10 pages.
PCT International Search Report and Written Opinion in International Appln. No. PCT/US2015/058834, dated Feb. 17, 2016, 13 pages.
PCT International Search Report in International Appln. No. PCT/US2015/058841, dated Feb. 23, 2016, 5 pages.
PCT Written Opinion in International Appln. No. PCT/US2015/058841, dated Feb. 23, 2016, 14 pages.
Peterson et al., "Bacterial Cell Surface Damage Due to Centrifugal Compaction," Applied and Environmental Microbiology, 78(1):120-125, Jan. 2012.
Shen et al., "High-throughput rare cell separation from blood samples using steric hindrance and inertial microfluidics," Lab Chip, 2014, DOI: 10.1039/C3LC51384J, Mar. 2014, 15 pages.
Tanyeri et al., "A microfluidic-based hydrodynamic trap: Design and implementation," Lab Chip, 11(10):1786-1794, May 2011.
Yang et al., "Sheathless elasto-inertial particle focusing and continuous separation in a straight rectangular microchannel," Lab Chip, Jan. 2011, 11(2):266-273.

\* cited by examiner

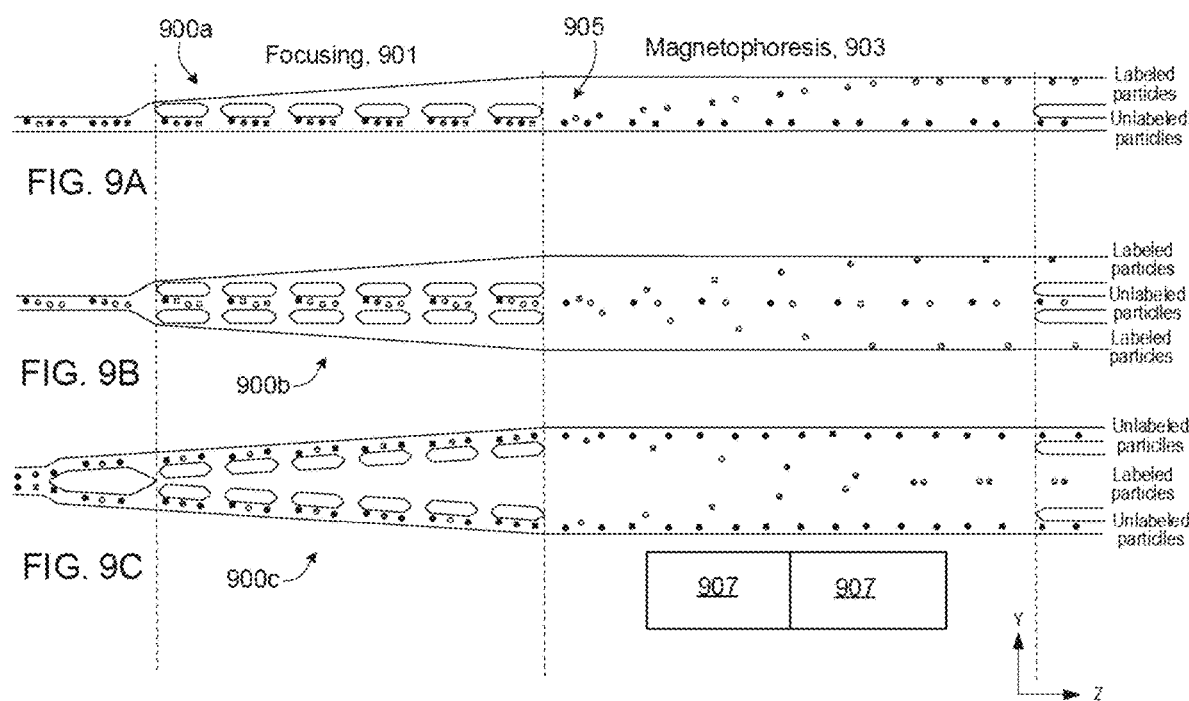

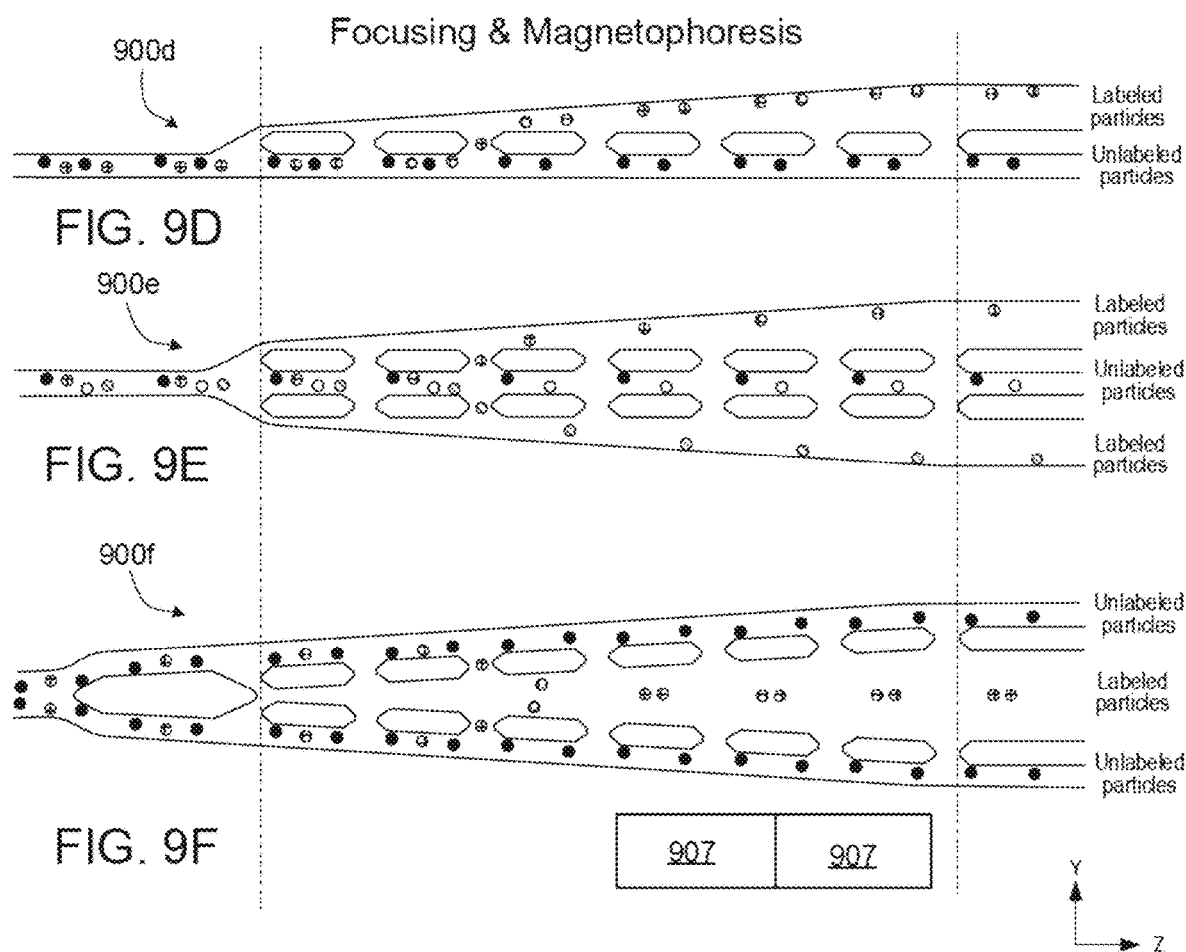

CONCENTRATING PARTICLES IN A MICROFLUIDIC DEVICE

CROSS-REFERENCE TO RELATED APPLICATIONS

This application is a continuation of U.S. application Ser. No. 17/335,510, filed on Jun. 1, 2021, which is a continuation of U.S. application Ser. No. 16/211,362, filed on Dec. 6, 2018, now Issued U.S. Pat. No. 11,052,393, which is a divisional of U.S. application Ser. No. 14/931,421, filed on Nov. 3, 2015, now Issued U.S. Pat. No. 10,150,116, which claims the benefit of U.S. Provisional Application No. 62/074,213, filed Nov. 3, 2014, and U.S. Provisional Application No. 62/074,315, filed Nov. 3, 2014, each of which is incorporated herein by reference in its entirety.

STATEMENT OF FEDERALLY SPONSORED RESEARCH

This invention was made with government support under Grant Nos. EB002503, and EB012493 awarded by the National Institutes of Health. The government has certain rights in the invention.

TECHNICAL FIELD

The present disclosure relates to concentrating particles in a microfluidic device.

BACKGROUND

Particle separation and filtration have been used in numerous applications across industries and fields. Examples of such applications include chemical process and fermentation filtration, water purification/wastewater treatment, sorting and filtering components of blood, concentrating colloid solutions, and purifying and concentrating environmental samples. Various macro-scale techniques have been developed for use in these applications including methods such as centrifugation and filter-based techniques. Typically, such techniques require systems that are large, bulky, and expensive and have complex moving components.

In certain cases, micro-scale techniques offer advantages over macro-scale techniques, in that scaling down allows the use of unique hydrodynamic effects for particle sorting and filtration, and thus eliminates the need for large systems with complex moving components. Moreover, micro-scale techniques offer the possibility of portable devices capable of performing sorting and filtration at much lower cost than larger macro-scale systems. However, typical micro-scale sorting and filtration devices may be limited in the amount of fluid they can handle over a specified period of time (i.e., low throughput), potentially placing such devices at a disadvantage to their macro-scale counterparts.

SUMMARY

The present disclosure is based, at least in part, on the discovery that if one carefully controls the geometries and dimensions of microfluidic devices one can manipulate not only the position of particles suspended within a fluid sample, but also portions of the fluid itself to enable substantial increases in particle concentration for large quantities of the fluid sample or to filter fluid samples of undesired particles. For example, careful control of the geometries and dimensions of a microfluidic device can, in certain implementations, be used to alter the concentration of particles within a fluid sample through shifting the particles across fluid streamlines.

In particular, through a combination of fluid extraction and inertial lift forces, it is possible to manipulate both particles and the fluid that carries them to alter the concentration of one or more types of particles within the fluid. For instance, a fluid containing particles may be introduced into a microfluidic channel having an array of rigid island structures separating the channel from an adjacent microfluidic channel. As fluid is extracted from the first microfluidic channel into the second microfluidic channel through gaps between the island structures, the particles are drawn nearer to the island structures. As the particles reach nearer to the island structures, the particles experience an inertial lift force away from the direction of fluid extraction such that the particles cross fluid streamlines and remain in the first microfluidic channel while the amount of fluid in the first microfluidic channel decreases (i.e., leading to an increase in particle concentration).

The combination of fluid extraction and inertial lift force enables a number of ways to manipulate fluids and particles. For example, particles may be shifted from one fluid to another. In another example, the combined fluid extraction and inertial lift forces may be used to focus particles to desired positions within a microfluidic channel. These and other applications may be scaled over large numbers of microfluidic channels to achieve high throughput increases in particle concentration with low device fabrication costs.

In general, in one aspect, the subject matter of the present disclosure can be embodied in microfluidic devices that have a first microfluidic channel, a second microfluidic channel extending along the first microfluidic channel, and a first array of islands separating the first microfluidic channel from the second microfluidic channel, in which each island is separated from an adjacent island in the array by an opening that fluidly couples the first microfluidic channel to the second microfluidic channel, in which the first microfluidic channel, the second microfluidic channel, and the islands are arranged so that a fluidic resistance of the first microfluidic channel changes relative to the fluidic resistance of the second microfluidic channel along a longitudinal section of the first microfluidic channel or the second microfluidic channel such that, during use of the microfluidic device, a portion of a fluid sample flowing in the first microfluidic channel or the second microfluidic channel is siphoned through one or more of the openings between adjacent islands.

In general, in another aspect, the subject matter of the present disclosure can be embodied in microfluidic devices including: a first microfluidic channel; a second microfluidic channel extending along the first microfluidic channel; and a first array of islands separating the first microfluidic channel from the second microfluidic channel, in which each island is separated from an adjacent island in the array by an opening that fluidly couples the first microfluidic channel to the second microfluidic channel, in which the first microfluidic channel, the second microfluidic channel, and the islands are arranged so that a fluidic resistance of the first microfluidic channel increases relative to a fluidic resistance of the second microfluidic channel along a longitudinal direction of the first microfluidic channel such that, during use of the microfluidic device, a portion of a fluid sample flowing through the first microfluidic channel passes through one or more of the openings between adjacent islands into the second microfluidic channel, and in which a width of the first microfluidic channel repeatedly alternates between a narrow region and an enlarged region along the longitudinal direction of the first microfluidic channel.

Implementations of the devices may have one or more of the following features. For example, in some implementations, the first microfluidic channel, the second microfluidic channel and the first array of islands are further arranged to, during use of the microfluidic device, substantially prevent multiple first types of particles in the fluid sample from propagating with the fluid through one or more of the openings between adjacent islands into the second microfluidic channel. The first microfluidic channel, the second microfluidic channel and the first array of islands can be arranged to, during use of the microfluidic device, impart an inertial lift force on the plurality of the first type of particle to prevent the multiple first types of particle from propagating with the fluid through one or more of the openings between adjacent islands into the second microfluidic channel. The first microfluidic channel, the second microfluidic channel and the first array of islands can be arranged to, during use of the microfluidic device, impart a bumping force on the plurality of the first type of particle to prevent the multiple first types of particle from propagating with the fluid through one or more of the openings between adjacent islands into the second microfluidic channel. A cross-sectional area of each opening through which the fluid passes from the first microfluidic channel into the second microfluidic channel can be larger than the first type of particle.

In some implementations, the increase in fluidic resistance of the first channel relative to the fluidic resistance of the second channel includes a change in a cross-sectional area of the first microfluidic channel or the second microfluidic channel along the longitudinal direction of the first microfluidic channel. The change in cross-sectional area of the second microfluidic channel can include an increase in the cross-sectional area of the second microfluidic channel relative to the cross-sectional area of the first microfluidic channel along the longitudinal direction. The change in cross-sectional area of the first microfluidic channel can include a decrease in the cross-sectional area of the first microfluidic channel relative to the cross-sectional area of the second microfluidic channel along the longitudinal direction.

In some implementations, the array of islands includes multiple openings and a size of the openings increases along the longitudinal direction of the first microfluidic channel. A size of each opening in the array can be greater than a size of a previous opening in the array.

In some implementations, at least one of the enlarged regions is aligned with a corresponding opening between the islands. The first microfluidic channel can have an approximately sinusoidal shape.

In some implementations, for each island, a contour of a first side of the island substantially matches a contour of a wall of the first channel facing the first side of the island.

In some implementations, the microfluidic devices further includes: a third microfluidic channel extending along the first microfluidic channel; and a second array of islands separating the first microfluidic channel and the third microfluidic channel such that the first microfluidic channel is between the second and third microfluidic channels, in which each island in the second array is separated from an adjacent island in the second array by an opening that fluidly couples the first microfluidic channel to the third microfluidic channel, and in which the third microfluidic channel, the first microfluidic channel, and the second array of islands are arranged so that the fluidic resistance of the first microfluidic channel increases relative to a fluidic resistance of the third microfluidic channel along the longitudinal direction of the first microfluidic channel such that, during use of the microfluidic device, a portion of a fluid sample flowing through the first microfluidic channel passes through one or more of the openings between adjacent islands of the second array of islands into the third microfluidic channel. The increase in fluidic resistance of the first channel relative to the fluidic resistance of the third channel can include a change in a cross-sectional area of the first microfluidic channel or the third microfluidic channel along the longitudinal direction of the first microfluidic channel.

In some implementations, the microfluidic devices further include: a third microfluidic channel extending along the second microfluidic channel; and a second array of islands separating the second microfluidic channel and the third microfluidic channel such that the second microfluidic channel is between the first and third microfluidic channels, in which each island in the second array is separated from an adjacent island in the second array by an opening that fluidly couples the second microfluidic channel to the third microfluidic channel, and in which the third microfluidic channel, the second microfluidic channel, and the second array of islands are arranged so that a fluidic resistance of the third microfluidic channel increases relative to the fluidic resistance of the second microfluidic channel along a longitudinal direction of the third microfluidic channel such that, during use of the microfluidic device, a portion of a fluid sample flowing through the third microfluidic channel passes through one or more of the openings between adjacent islands of the second array of islands into the second microfluidic channel.

In some implementations, the microfluidic devices further include: a first inlet channel; and a second inlet channel, in which each of the first inlet channel and the second inlet channel is fluidly coupled to the first microfluidic channel and the second microfluidic channel. In some implementations, the microfluidic devices further include: a first inlet channel; and a second inlet channel, in which each of the first inlet channel and the second inlet channel is fluidly coupled to the first microfluidic channel, the second microfluidic channel and the third microfluidic channel.

In some implementations, the first microfluidic channel, the second microfluidic channel, and the first array of islands correspond to a combined inertial focusing and fluid siphoning region, in which the microfluidic device includes multiple combined inertial focusing and fluid siphoning regions arranged in parallel.

In some implementations, the microfluidic devices further include one or more magnets establishing a magnetic field gradient across the first and/or second microfluidic channel.

In some implementations, the first microfluidic channel and the second microfluidic channel are arranged in a spiral configuration.

In some implementations, the first array comprises at least three islands.

In general, in another aspect, the subject matter of the present disclosure can be embodied in microfluidic devices including: a first microfluidic channel; a second microfluidic channel extending along the first microfluidic channel; and a first array of islands separating the first microfluidic channel from the second microfluidic channel, in which each island is separated from an adjacent island in the array by an opening that fluidly couples the first microfluidic channel to the second microfluidic channel, in which the first microfluidic channel, the second microfluidic channel, and the islands are arranged so that a fluidic resistance of the first microfluidic channel increases relative to a fluidic resistance of the second microfluidic channel along a longitudinal direction of the first microfluidic channel such that, during use of the microfluidic device, a portion of a fluid sample flowing through the first microfluidic channel passes through one or more of the openings between adjacent islands into the second microfluidic channel.

In general, in another aspect, the subject matter of the present disclosure can be embodied in methods of changing a concentration of particles within a fluid sample, the methods including: flowing a fluid sample containing multiple first types of particle into a microfluidic device, in which the microfluidic device includes a first microfluidic channel, a second microfluidic channel extending along the first microfluidic channel, and a first array of islands separating the first microfluidic channel from the second microfluidic channel, in which the first microfluidic channel, the second microfluidic channel, and the islands are arranged so that a fluidic resistance of the first microfluidic channel increases relative to a fluidic resistance of the second microfluidic channel along a longitudinal direction of the first microfluidic channel such that a portion of the fluid sample flowing through the first microfluidic channel passes through one or more of the openings between adjacent islands into the second microfluidic channel without the first type of particle, and in which a width of the first microfluidic channel repeatedly alternates between a narrow region and an enlarged region along the longitudinal direction of the first microfluidic channel such that inertial focusing causes the multiple first types of particle to be focused to one or more streamlines of the fluid sample within the first channel.

Implementations of the methods may have one or more of the following features. For example, in some implementations, a concentration of the first type of particle increases within the fluid sample remaining in the first microfluidic channel.

In some implementations, the microfluidic device includes a third microfluidic channel extending along the second microfluidic channel and a second array of islands that separates the second microfluidic channel from the third microfluidic channel, in which a fluidic resistance of the third microfluidic channel increases relative to the fluidic resistance of the second microfluidic channel along a longitudinal direction of the third microfluidic channel such that a portion of the fluid sample flowing through the third microfluidic channel passes through openings between islands in the second array into the second microfluidic channel without the first type of particle, and in which a width of the third microfluidic channel repeatedly alternatives between a narrow region and an enlarged region along the longitudinal direction of the third microfluidic channel such that inertial focusing causes the plurality of the first type of particle to be focused to one or more streamlines of the fluid sample within the third channel. A concentration of the first type of particle can increase within the fluid sample remaining in the third microfluidic channel.

In some implementations, the microfluidic device includes a third microfluidic channel extending along the first microfluidic channel and a second array of islands that separates the first microfluidic channel from the third microfluidic channel, in which the fluidic resistance of the first microfluidic channel increases relative to the fluidic resistance of the third microfluidic channel along the longitudinal direction of the third microfluidic channel such that a portion of the fluid sample flowing through the first microfluidic channel passes through the openings between islands in the second array into the third microfluidic channel without the first type of particle.

In some implementations, at least one of the first type of particles is bound to a magnetic bead, and the methods further include exposing the fluid sample to a magnetic field gradient, in which the magnetic field gradient guides the at least one particle bound to a magnetic bead away from one or more of the openings between adjacent islands in the first array.

In some implementations, the fluid sample contains multiple second types of particle, in which the second types of particles are bound to magnetic beads, and the methods further include exposing the fluid sample to a gradient in a magnetic field, in which the gradient in the magnetic field deflects the second type of particles that are bound to magnetic beads away from the first type of particle such that the second type of particle propagates with the fluid portion through one or more of the openings of the first array.

In some implementations, the fluid sample has a dynamic viscosity that varies with shear rate, and the method further includes driving the fluid sample through the first microfluidic channel at a volumetric flow rate that results in the formation of a localized streamline at or near a center of the first microfluidic channel, in which the multiple first types of particles are focused into the localized streamline. The fluid sample can include a drag-reducing polymer added to a Newtonian fluid. The drag-reducing polymer can include hyaluronic acid (HA).

In some implementations, the particle to fluid concentration at an output of the first microfluidic channel is greater than 10 times and less than 5000 times the particle to fluid concentration prior to entering the first microfluidic channel.

In some implementations, the methods further include collecting the multiple first types of particle at an output of the first microfluidic channel.

In some implementations, the first type of particle has an average diameter between about 1 μm and about 100 μm.

In some implementations, a size of each opening between the islands is greater than the average diameter of the first type of particle.

Implementations of the subject matter described herein provide several advantages. For example, in some implementations, the subject matter described herein can be used to isolate particles within a continuously flowing fluid, focus particles within a continuously flowing fluid, increase the concentration of particles within a continuously flowing fluid without the need for centrifugation, and/or obtain purified fluid samples with low particle concentration. In some implementations, the subject matter described herein can be used to shift particles from one fluid to another fluid. The continuous flow microfluidic techniques described herein may offer high volumetric capacity and throughput, substantial and tunable fluid volume reduction, and high particle yields with inexpensive and simple instruments that can be implemented into various point-of-care devices. In particular, the presently described techniques may offer significant advantages over existing centrifugation techniques, especially in applications where the size and expense of centrifugation is prohibitive. In some implementations, the presently described techniques also may provide streamlined processing and simple integration with other microfluidic modules. For clinical applications, the systems described herein may be configured as both self-contained and disposable. In contrast, for bioprocessing/industrial applications, the devices may be configured for continuous flow/processing.

For the purposes of this disclosure, channel refers to a structure in which a fluid may flow.

For the purposes of this disclosure, microfluidic refers to a fluidic system, device, channel, or chamber that generally have at least one cross-sectional dimension in the range of about 10 nm to about 10 mm.

For the purposes of this disclosure, the terms gap or opening refer to an area in which fluids or particles may flow. For example, a gap or opening may be a space between two obstacles in which fluids flow.

For the purposes of this disclosure, rigid island structure refers to a physical structure through which a particle generally cannot penetrate.

For the purposes of this disclosure, volume reduction means processing a suspension of cells/particles such that the product of the process has a higher concentration (and therefore smaller volume) of the cells/particles than the input.

For the purposes of this disclosure, a particle-free layer is understood to be an elongated region of a continuously flowing fluid sample within a microfluidic device that is substantially free of one or more different types of particles.

For the purposes of this disclosure, absolute particle yield is understood to mean the total number of particles in the product divided by the total number particles in the input.

For the purposes of this disclosure, relative yield is understood to mean the total number of particles in the product divided by the total number of particles in the output (i.e., product plus waste).

For the purposes of this disclosure, length fraction is understood to mean the fraction of that stream occupied by particles (as opposed to space between particles).

For the purposes of this disclosure, fluidic resistance refers to the ratio of pressure drop across a channel (e.g., a microfluidic channel) to the flow rate of fluid through the channel.

Particles within a sample can have any size which allows them to transported within the microfluidic channel. For example, particles can have an average hydrodynamic size that is between 1 μm and 100 μm. The particle size is limited only by channel geometry; accordingly, particles that are larger and smaller than the above-described particles can be used. The size of particles (e.g., cells, eggs, bacteria, fungi, virus, algae, any prokaryotic or eukaryotic cells, organelles, exosomes, droplets, bubbles, pollutants, precipitates, organic and inorganic particles, magnetic beads, and/or magnetically labeled analytes), such as the average hydrodynamic particle size or average diameter, can be determined using standard techniques well known in the field.

Unless otherwise defined, all technical and scientific terms used herein have the same meaning as commonly understood by one of ordinary skill in the art to which this invention belongs. Although methods, materials, and devices similar or equivalent to those described herein can be used in the practice or testing of the present invention, suitable methods, materials and devices are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features, objects, and will be apparent from the description, drawings, and claims.

BRIEF DESCRIPTION OF THE DRAWINGS

FIGS. 9A-9C are schematics illustrating examples of microfluidic systems in which a particle shifting area is fluidly coupled to a magnetophoresis area.

FIGS. 9D-9F are schematics illustrating examples of microfluidic systems in which a particle shifting area and a magnetophoresis area are combined.

DETAILED DESCRIPTION

Figure 1:
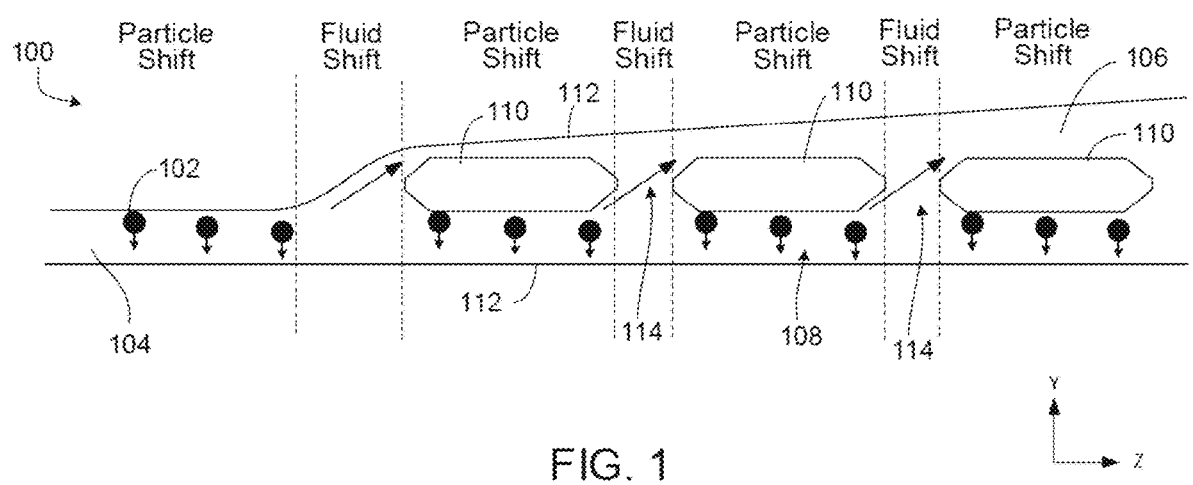
FIG. 1 is a schematic illustrating a top view of an example of a microfluidic device capable of shifting the position of particles within and across fluid streamlines.

Interactions among particles within a fluid (e.g., cells, e.g., blood cells in general as well as fetal blood cells in maternal blood, bone marrow cells, and circulating tumor cells (CTCs), sperm, eggs, bacteria, fungi, virus, algae, any prokaryotic or eukaryotic cells, cell clusters, organelles, exosomes, droplets, bubbles, pollutants, precipitates, organic and inorganic particles, beads, bead labeled analytes, magnetic beads, and/or magnetically labeled analytes), the fluids in which the particles travel (e.g., blood, aqueous solutions, oils, or gases), and rigid structures can be controlled to perform various microfluidic operations on both the particles and fluid. In particular, such interactions may entail shifting the particles across fluid streamlines, through either the displacement of the fluid or the particles themselves. Examples of microfluidic operations that can be performed by controlling these interactions include, but are not limited to, increasing the concentration of particles in a carrier fluid, reducing the volume of a fluid sample, reducing the concentration of particles within a fluid, shifting particles from one carrier fluid to another fluid, separating particles within a fluid based on particle size (e.g., average diameter), focusing particles within a carrier fluid to a single-streamline (or to multiple different streamlines), precise positioning of particles at any position within a microchannel, and mixing (defocusing) particles. Moreover, any of the above operations can be executed simultaneously with other techniques (e.g., magnetic sorting) to enhance the operation's effectiveness.

Several different mechanisms can be employed to create the forces capable of shifting particles across fluid streamlines. Any of the following techniques may be used individually or in combination to induce particle shifting within a fluid. A first type of force is referred to as "bumping" (also called deterministic lateral displacement (DLD)). Bumping is direct interaction between a rigid wall of a structure and a particle that arises due to the size of the particle relative to the wall. Since the center of a particle having radius $r_p$ cannot pass closer to an adjacent structure than $r_p$, if the particle center lies on a streamline that is less than $r_p$ from the structure, the particle will be bumped out by the structure to a distance that is at least $r_p$ away. This bumping may move the particle across fluid streamlines.

Another type of force is called inertial lift force (also known as wall force or wall induced inertia). The inertial lift force is a fluidic force on a particle that arise when then the particle and fluid flow near a wall. Though not well understood, the inertial lift force is a repulsive force arising due to a flow disturbance generated by the particle when the particle nears the wall. In contrast to bumping, the inertial lift force is a fluidic force on a particle, not a force due to contact with a rigid structure. A particle flowing near a micro-channel wall experiences an inertial lift force normal to the wall. At high flow rates, the inertial lift force is very strong and can shift the particle across streamlines.

Another type of force is a result of pressure drag from Dean flow. Microfluidic channels having curvature can create additional drag forces on particles. When introducing the curvature into rectangular channels, secondary flows (i.e., Dean flow) may develop perpendicular to the direction of a flowing stream due to the non-uniform inertia of the fluid. As a result, faster moving fluid elements within the center of a curving channel can develop a larger inertia than elements near the channel edges. With high Dean flow, drag on suspended particles within the fluid can become significant.

Another type of particle shifting occurs with high Stokes number flow. The Stokes number (Stk) describes how quickly a particle trajectory changes in response to a change in fluid trajectory. For Stk greater than 1, a lag exists between the change in fluid trajectory and the change in particle trajectory. Under high Stokes flow conditions (e.g., a Stokes number greater than about 0.01), changing the fluid flow direction can be used to force particles across streamlines. Further details on Dean flow and high Stokes number can be found, for example, in U.S. Pat. No. 8,186,913, which is incorporated herein by reference in its entirety. In both high Stokes flow applications and Dean flow applications, the fluid displacement causes the particles to cross fluid streamlines.

Other techniques for shifting particles include viscoelastic and inertio-elastic focusing. Details on those methods can be found in "Sheathless elasto-inertial particle focusing and continuous separation in a straight rectangular microchannel," Yang et al., Lab Chip (11), 266-273, 2011, "Single line particle focusing induced by viscoelasticity of the suspending liquid: theory, experiments and simulations to design a micropipe flow-focuser," D'Avino et al., Lab Chip (12), 1638-1645, 2012, and "Inertio-elastic focusing of bioparticles in microchannels at high throughput," Lim et al., Nature Communications, 5 (5120), 1-9, 2014, each of which is incorporated herein by reference in its entirety.

The foregoing techniques for shifting particles are "internal," in that they use fluid flow and/or structures of the microfluidic channel itself to generate the forces necessary to shift particles across streamlines. In some cases, other external mechanisms can also be used in conjunction with one or more of the internal forces to alter the course of particles traveling within a fluid. For example, in some cases, externally applied magnetic forces, gravitational/centrifugal forces, electric forces, or acoustic forces may be used to cause a shift in particle position across fluid streamlines. Further information on how to apply such forces can be found, e.g., in WO 2014/004577 titled "Sorting particles using high gradient magnetic fields,", U.S. Pat. No. 7,837, 040 titled "Acoustic focusing," WO 2004/074814 titled "Dielectrophoretic focusing," and "Microfluidic, Label-Free Enrichment of Prostate Cancer Cells in Blood Based on Acoustophoresis," Augustsson et al., Anal. Chem. 84(18), Sep. 18, 2012, The present disclosure focuses primarily on combining inertial lift forces with periodic fluid extraction to shift particles across fluid streamlines to modify the concentration of and/or to filter particles in a fluid, though it should be understood that inertial lift forces may be replaced with or used in addition to other forces, such as those described above. As an example of combined inertial, particle containing fluids may be introduced into a microfluidic channel having an array of rigid island structures separating the channel from an adjacent microfluidic channel. As fluid is extracted from the first microfluidic channel into the second microfluidic channel through gaps between the island structures, the particles are drawn nearer to the island structures. As the particles reach nearer to the island structures, the particles experience a repulsive force (e.g., an inertial lift force) away from the direction of fluid extraction such that the particles cross fluid streamlines. The combination of fluid extraction and the repulsive forces may be used to perform positioning of particles, increasing the concentration of particles within a fluid, decreasing the concentration of particles within a fluid, particle mixing, fluid mixing, and/or shifting of fluids across particle streams, among other operations.

The mechanisms for shifting particles may be size-based and therefore can be used to perform size-based manipulation of particles (e.g., based on the average diameter of the particles). Through the repeated shifting of particles and/or displacement of fluid using any of the above-mentioned techniques, various different microfluidic operations may be performed, such as focusing particles to one or more fluid streamlines, increasing the concentration of particles within a fluid, performing volume reduction of a fluid, filtering particles from a fluid, and/or mixing different particles from different fluid streams. In general, "focusing" particles refers to re-positioning the particles across a lateral extent of the channel and within a width that is less than the channel width. For example, the techniques disclosed herein can localize particles suspended in a fluid within a length of the channel having a width of 1.05, 2, 4, 6, 8, 10, 20, 30, 40, 50, 60, 70, 80, 90, or 100 times the average diameter of the particles. In some implementations, the particles are focused to a streamline of a fluid. In some implementations, a streamline defines a width that is substantially equal to or slightly greater than a hydraulic diameter of the particle. Particles may have various sizes including, but not limited to, between about 1 µm and about 100 µm in average diameter.

Altering Particle Concentration Using Inertial Lift Forces

FIG. 1 is a schematic that illustrates a top view of an example of a microfluidic device 100 capable of shifting the position of particles 102 across fluid streamlines while the fluid propagates through the microfluidic device 100. As will be explained, the particle shifting across fluid streamlines relies on the inertial lift forces experienced by particles as fluid is periodically extracted from a microfluidic channel, though other repulsive forces may be used in place of or in addition to inertial lift forces. For reference, a Cartesian coordinate system is shown, in which the x-direction extends into and out of the page.

During operation of the device 100, a fluid carrying the particles 102 is introduced through an inlet microfluidic channel 104. In this and other implementations of the particle shifting devices, the fluid can be introduced through the use of a pump or other fluid actuation mechanism. The inlet channel 104 splits into two different fluid flow channels (second microfluidic channel 106 and first microfluidic channel 108 substantially parallel to the second microfluidic channel 106) that are separated by a 1-dimensional array of rigid island structures 110. The 1-dimensional array of island structures 110 extends substantially in the same direction as the flow of the fluid through the second and first microfluidic channels. Each island structure 110 in the array is separated from an adjacent island 110 by an opening or gap 114 through which fluid can flow. Each gap 114 in the example of FIG. 1 has the same distance between adjacent islands 110. In other implementations, different gaps can have different distances between adjacent islands 110. For example, in some implementations, a length of each subsequent opening (e.g., as measured along the fluid propagation direction—the z-direction in FIG. 1) in the first array is greater than a size of a previous opening in the array. Furthermore, although a 1-dimensional array is shown in FIG. 1, the islands 110 may be arranged in different configurations including, for example, a two-dimensional array of islands. The boundaries of the fluid flow regions within the microfluidic channels are defined by the device walls 112 and the walls of the islands 110.

As the fluid propagates substantially along the z-direction (i.e., the longitudinal direction) from the inlet channel 104 to the channels (106, 108), particles 102 experience a force (in this example, an inertial lift force) that causes the particles 102 to shift across fluid streamlines and travel along the first microfluidic channel 108. These inertial lift forces are in the negative y-direction (see short arrows adjacent to each particle 102 in FIG. 1).

For instance, when a particle 102 is located in the inlet channel 104 and approaches the top wall 112, the particle experiences an inertial lift force that pushes the particle down toward the first microfluidic channel 108. Once in the first microfluidic channel 108, the particle 102 may approach a wall of the first island 110, such that it again experiences an inertial lift force pushing the particle 102 down, maintaining the particle within the first microfluidic channel 108. The repeated application of the inertial lift force to the particle 102 in each of the "particle shift" regions shown in FIG. 1 thus serves to separate/filter the particle from the fluid propagating through the second microfluidic channel 106.

At the same time, portions of the fluid traveling in the first microfluidic channel 108 are extracted (e.g., siphoned)/pass into the second microfluidic channel at one or more "fluid shift" regions (see FIG. 1) in the device 100. In the example of FIG. 1, each fluid shift region corresponds to an opening or gap that extends between the first microfluidic channel 108 and the second microfluidic channel 106. Each "fluid shift" region primarily allows fluid to be extracted from the first microfluidic channel 108 into the second microfluidic channel 106. The movement of fluid into the gaps tends to pull the particles 102 toward the gaps as well, since the particles follow the fluid streamlines. However, as the particles move closer to the gaps 114, they approach the island structures 112, which impart an inertial lift force causing the incident particles to cross fluid streamlines in a direction away from the gaps 114. That is, the particles 102 shift from a fluid streamline passing into the second microfluidic channel 106 to a fluid streamline that continues to flow in the first microfluidic channel 108. As a result, the particles 102 continue to propagate in the first microfluidic channel 108 and are not shifted into the second microfluidic channel 106 with the fluid. If there were no fluid shifting from the first microfluidic channel 108 to the second microfluidic channel 106, the particles would migrate as a result of inertial focusing toward equilibrium focusing positions where the inertial lift force and shear gradient force are balanced. However, by shifting the fluid across the channels, the particles 102 tend to follow the fluid toward areas where the inertial lift force is much stronger than the shear gradient force, thus causing the particles to shift across streamlines in a very efficient and controlled manner.

In the present example, the fluid is extracted through the fluid shift regions as a result of decrease in fluidic resistance along a longitudinal section of the fluid shift region. That is, for a fluid of constant viscosity, the gaps 114 between adjacent islands 110 increase the channel area through which the fluid can flow, resulting in a reduced fluidic resistance. As fluid propagates through the device 100 and arrives at a gap 114, a portion of the fluid will flow into the gap 114 and subsequently into the second microfluidic channel 106 (i.e., the fluid portion is extracted into channel 106). The decrease in fluidic resistance also can occur as a result of the increasing channel width in the second microfluidic channel 106. In particular, the second microfluidic channel wall 112 is slanted at an angle away from the islands so that the width of the second microfluidic channel 106 increases along the channel's longitudinal direction (i.e., in the direction of fluid propagation or the positive z-direction), thus causing a decrease in fluidic resistance. Any increase in the cross-sectional area of the channel 106 along the longitudinal direction of the first microfluidic channel, not just an increase in width, also can be employed to reduce the fluidic resistance. Alternatively, or in addition, the fluid may experience an increase in fluidic resistance in channel 108 relative to the fluidic resistance of channel 106 (e.g., through a decrease in the cross-sectional area of the channel 108 along the longitudinal direction). Thus, it may be said that the fluid is extracted in response to a change in the relative fluidic resistance between the second and first microfluidic channels. The change in the relative fluidic resistance may occur over the entire particle sorting region or over a portion of the sorting region that is less than the entire particle sorting region. The change in the relative fluidic resistance may occur over along the direction of the fluid flow through the particle sorting region (e.g., along a longitudinal direction of the particle sorting region as shown in FIG. 1).

With progressively lower fluidic resistance at the gaps 114 and/or in channel 106, greater amounts of fluid flow into the second microfluidic channel 106. Furthermore, the repeated shifting of fluid into the second channel 106 reduces the amount of fluid in the first channel 108. This constant fluid extraction thus increases the particle-to-fluid concentration in the first channel 108, while decreasing the concentration of particles in the second microfluidic channel 106, such that the fluid in the second microfluidic channel 106 is "filtered" or "purified." In some implementations, the particle shifting techniques disclosed herein may be capable of increasing the particle concentration from an initial fluid sample by up to 10, 25, 50, 75, 100, 200, 300, 400, or 500 times the initial particle to fluid concentration. Such concentration increases can result in particle yields from fluid samples of up to 90%, up to 95%, up to 99% or even 100%.

In some implementations, the increases in particle concentrations may be achieved using multiple microfluidic devices configured to employ the particle shifting techniques disclosed herein. For example, the output of a first microfluidic device configured to increase the particle concentration of an incoming fluid sample by 10× may be coupled to an input of a second microfluidic device configured to increase the particle concentration of an incoming fluid sample by 50X, for an overall increase in particles concentration from the initial fluid sample of 500×.

In addition to increasing particle concentration, the repeated particle shifting may also be used to focus the particles along one or more desired positions/streamlines within the fluid propagating through the lower channel 108. For instance, as previously explained, portions of fluid may be extracted from an initial microfluidic channel into one or more parallel microfluidic channels. In some instances, the parallel microfluidic channels containing the extracted fluid then may be re-combined with the initial microfluidic channel downstream so that the particles are confined to designated streamlines in a single channel. An advantage of this technique of combining fluid shifting with inertial lift force is that particles may be focused to desired positions within the downstream channel (e.g., near the channel wall, at the middle of the channel, or halfway between the channel wall and the middle of the channel, among other positions) by controlling how much fluid is removed from each side of the initial channel, providing increased flexibility to the design and use of microfluidic devices. In contrast, for microfluidic systems based primarily on inertial focusing, one cannot choose the position of the focused stream within the channel.

The resulting concentrated and focused particle streamline may be coupled to a separate processing region of the microfluidic device 100 or removed from the device 100 for additional processing and/or analysis. Likewise, the "filtered" fluid in the second channel 106 may be coupled to a separate region of the microfluidic device 100 or removed from the device 100 for additional processing and/or analysis. In some implementations, the particles 102 entering the device 100 are "pre-focused" to a desired fluid streamline position that is aligned with the first microfluidic channel 108. By pre-focusing the particles 102 to a desired position, the probability that particles inadvertently enter into the second microfluidic channel 106 can be reduced.

Figure 2:
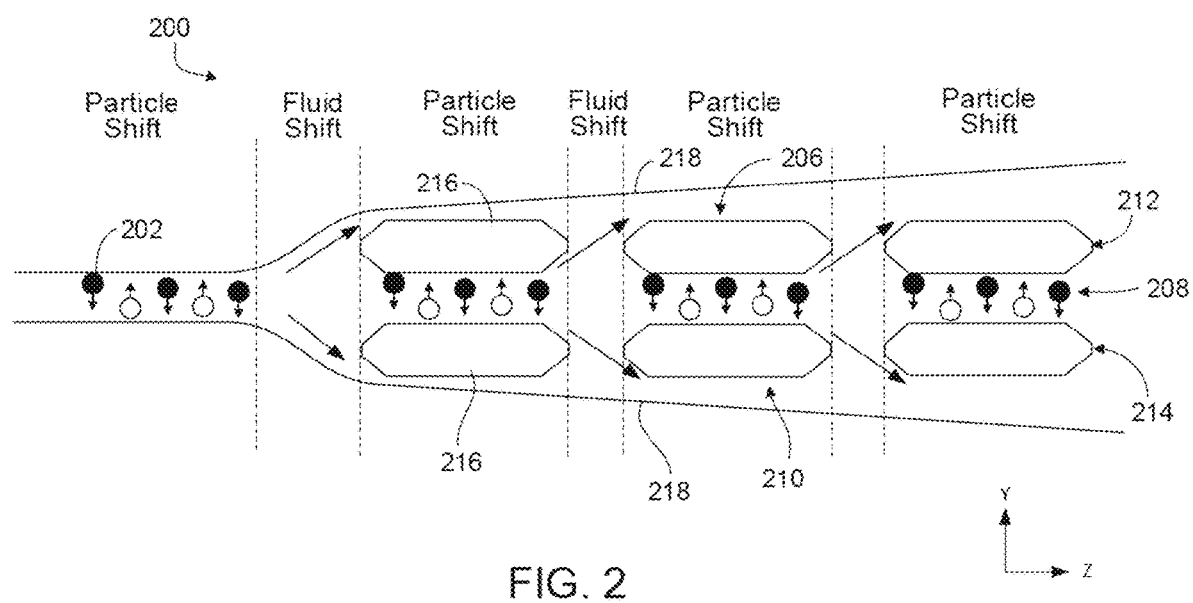
FIG. 2 is a schematic illustrating a top view of an example of a device for particle and fluid shifting, in which a particle shifting area includes two different microfluidic channels for extracting fluid.

Other microfluidic device configurations different from the implementation shown in FIG. 1 also may be used to concentrate particles based on repeated particle and fluid shifting. For example, FIG. 2 is a schematic that illustrates an example of a device 200 for particle and fluid shifting, in which the particle shifting area includes two different microfluidic channels for extracting fluid, rather than one microfluidic channel. The device 200 includes an inlet microfluidic channel 204 that is fluidly coupled to a particle shifting region that has three different fluid flow regions (an second microfluidic channel 206, a first microfluidic channel 208, and a third microfluidic channel 210). The second microfluidic channel 206 is separated from the first microfluidic channel 208 by a first array 212 of islands 216. The third microfluidic channel 210 is separated from the first microfluidic channel 208 by a second array 214 of islands 216. Each adjacent island in the first array 212 and each adjacent island in the second array 214 is separated by a gap for fluid shifting. The boundaries of the microfluidic channels are defined by the device walls 218 and the walls of the islands. The microfluidic channel walls 218 are slanted at angles away from the islands so that the widths of the second and third microfluidic channels (206, 210) increase along the fluid propagation direction (i.e., the positive z-direction), thus causing a decrease in fluidic resistance in each channel.

The device 200 operates in a similar manner to the device 100. In particular, as fluid propagates substantially along the z-direction from the inlet channel 204 to the channels (206, 208, 210), particles 202 within the fluid experience inertial lift forces in the "particle shift" regions upon approaching the walls of the inlet channel 204 and the walls of the island structures 216. The inertial lift forces in the inlet channel 204 push the particles 202 toward the center of the fluid flow (i.e., the inertial lift forces "focus" the particles toward central fluid streamlines), such that they primarily flow into the first microfluidic channel 208. Once the particles 202 enter the first microfluidic channel 208, they experience inertial lift forces from the island structures 216 that continue to focus the particles 202 along one or more central streamlines extending through the channel 208. At the same time, fluid is extracted into the second and third microfluidic channels (206, 210) in the "fluid shift" regions due to the reduced fluidic resistance. The combination of the fluid shift regions and the particle shift regions serve to focus particles from the incoming fluid into the first channel 208, while increasing the concentration of the particles at the same time. Any of the resulting fluid streams (from the second, first, or third channels) may be coupled to a separate region of the microfluidic device 200 or removed from the device 200 for additional processing or analysis. In some implementations, the variation in size/fluidic resistance of the second and third channels can be set so as to ensure that equal amounts of fluid flow in from the third channel and out the second channel at each unit.

Figure 3:
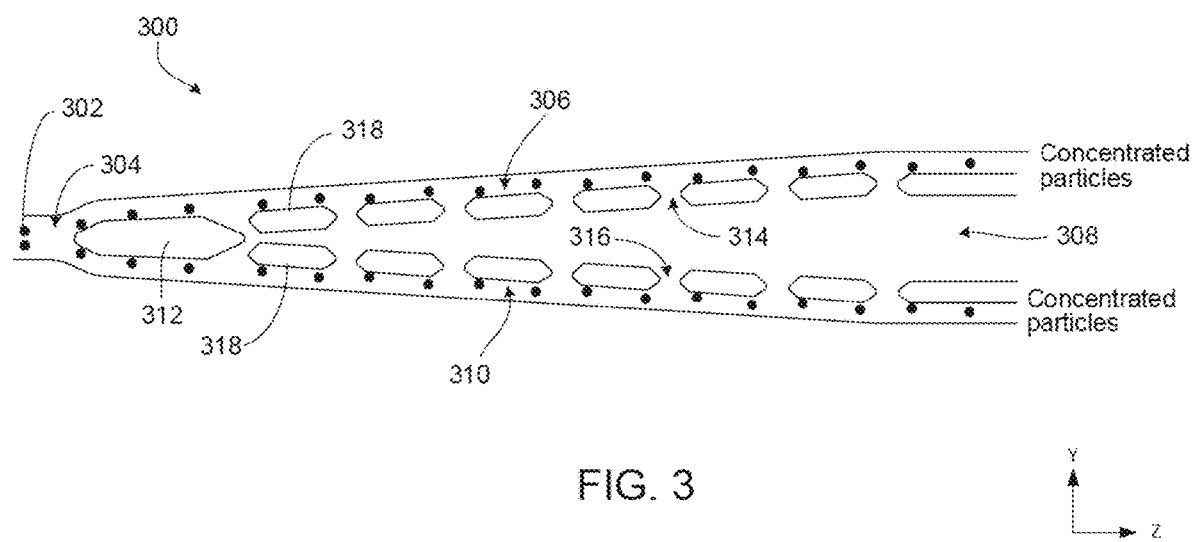
FIG. 3 is a schematic illustrating a top view of an example of a device in which particle shifting concentrates particles from one stream along two different microfluidic channels.

In some cases, particle and fluid shifting can be used to create multiple different streams of focused/concentrated particles. For instance, FIG. 3 is a schematic of a device 300 in which particle shifting concentrates particles from one stream along two different microfluidic channels. The device 300 includes an inlet microfluidic channel 304 that is fluidly coupled to two different fluid flow regions (a second microfluidic channel 306 and a third microfluidic channel 310). A single island structure 312 positioned at the coupling point between the inlet channel 404 and the second and third channels (306, 310) splits fluid propagating from the inlet channel 304 into two streams: one propagating along the second channel 306 and one propagating along the third channel 310. Downstream from the first island structure 312, the second microfluidic channel 306 is separated from the third microfluidic channel 310 by both a first array 314 of islands 318 and a second array 316 of islands 318. Each adjacent island in the first array 314 and each adjacent island in the second array 316 is separated by a gap for fluid shifting.

During operation of the device 300, a fluid containing particles 302 enters from the inlet channel 304. The fluid is separated by island 312 causing the fluid and the particles within the fluid to flow into either the second microfluidic channel 306 or the third microfluidic channel 310. Once the particles 302 have entered the second and third channels (306, 310), the particles remain concentrated within those channels due to repeated particle shifting (e.g., as a result of inertial lift forces) that occurs when the particles 302 approach the islands 318. A first microfluidic channel 308 is used to repeatedly extract fluid from the second and third channels (306, 310). In particular, the first channel 308 progressively increases in width, resulting in a lower fluidic resistance. Fluid is extracted from the second and third channels (306, 310) at the gaps between the islands 318 and follows this path of lower resistance. The device 300 thus takes a fluid containing randomly distributed particles and focuses/concentrates those particles into two separate streamlines in the second and third microfluidic channels 306, 310. The resulting particle streamlines and may be coupled to separate outputs for additional processing or analysis.

Figure 4:
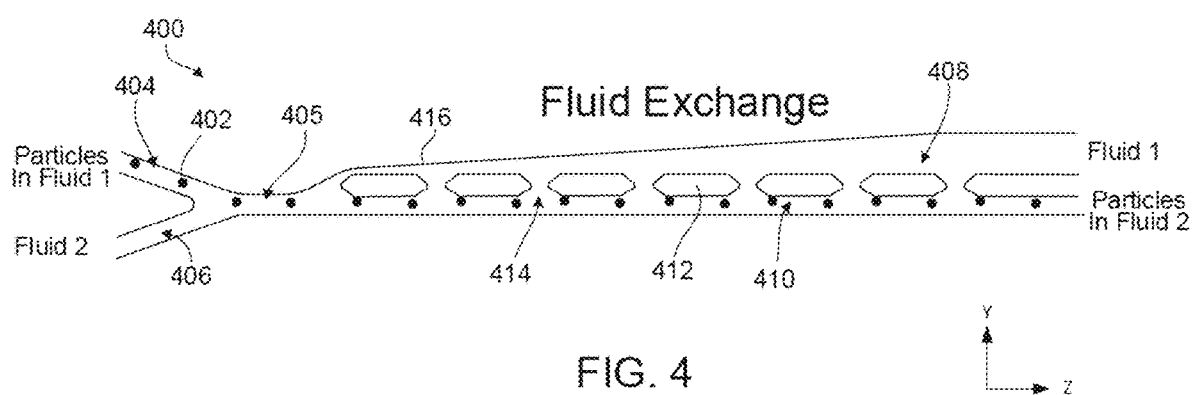
FIG. 4 is a schematic illustrating a top view of an example of a device capable of shifting particles from one carrier fluid to another carrier fluid.

The particle and shifting techniques described herein also may be used to shift particles from a first fluid to a second different fluid, where the concentration of the particles in the second fluid can be increased. FIG. 4 is a schematic that illustrates an example of a device 400 capable of shifting particles from one carrier fluid to another. The device 400 that includes two inlet microfluidic channels (404, 406) coupled to a single microfluidic channel 405 for merging the fluids. The merging channel 405 is, in turn, coupled to a particle shifting area that includes two different flow regions (second microfluidic channel 408 and first microfluidic channel 410). The second microfluidic channel 408 is separated from the first microfluidic channel 410 by an array of island structures 412, in which each island 412 is separated from an adjacent island 412 by a gap 414 for fluid shifting. In addition, the top wall 416 of the second microfluidic channel 408 is slanted at an angle away from the islands 412 in order to decrease the fluidic resistance between the second and first microfluidic channels along the downstream fluid direction.

During operation of the device 400, a first fluid ("Fluid 1") containing particles 402 is introduced in the first inlet channel 404 and a second fluid ("Fluid 2") having no particles is introduced into the second inlet channel 406. Assuming the fluids are introduced at flow rates corresponding to low Reynolds numbers (and thus laminar flow), there is little mixing between the two different fluids in the merge region 405, i.e., the two fluids essentially continue flowing as layers adjacent to one another. The fluid pathway within the merge region 405 is aligned with the fluid pathway of the first microfluidic channel 410 such that the merged fluids primarily flow into the first channel 410. As the two fluids enter the first microfluidic channel 410, the particles 402 within the first fluid experience inertial lift forces from the island structures 412 that are transverse to the direction of flow and that keep the particles 402 within the first microfluidic channel.

At the same time, the increasing width of the second microfluidic channel 408 (due to the slanted channel wall 416) decreases the fluidic resistance in the openings 414 between the channels, such that portions of the first fluid are extracted into the second channel 408 at each gap between the islands 412. Because the first fluid flows as a layer above the second fluid, it is primarily the first fluid that is extracted into the second channel 408 from the first channel 410. After propagating for a sufficient distance past the islands 412, most of the first fluid is extracted into the second channel 408, whereas the particles 402 and most of the second fluid remain in the first channel 410. Accordingly, the microfluidic device configuration shown in FIG. 4 is useful for transferring particles from one fluid to a second different fluid. In some implementations, the propagation distance is long enough so that the second fluid also is extracted into the second microfluidic channel 408. In that case, the concentration of the particles 402 in the first microfluidic channel 410 can be increased. Although the implementation shown in FIG. 4 includes two inlet channels, additional inlet channels may be coupled to the microfluidic channels used for altering the particle concentration.

The microfluidic devices shown in FIGS. 1-4 implement particle shifting across fluid streamlines using inertial lift forces from the microfluidic channel walls and from the periodic arrays of island structures. Techniques other than inertial lift force may be used to shift particles across fluid streamlines. For example, internal repulsive forces arising due to bumping against the island structures, high Dean flow and/or high Stokes flow, such as inertial focusing, can be used to shift particles across fluid streamlines. Alternatively, or in addition, external forces such as magnetic forces, acoustic forces, gravitational/centrifugal forces, and/or electrical forces may be used to shift particles across fluid streamlines.

Additionally, the shape of the rigid island structures that separate different flow regions is not limited to the shapes shown in FIGS. 1-4. For example, the rigid island structures may have shapes similar to posts, cuboids, or other polyhedrons in which the top and bottom faces are, or can be, congruent polygons. In some circumstances, such as at high flow rates, it is advantageous to use islands with streamlined, tapered ends (such as the shape of the island structures in FIGS. 1-4), as the taper helps minimize the formation of flow re-circulations (eddies) that disrupt flow in unpredictable and undesirable ways. Other shapes for the rigid island structures are also possible. The long axis of the rigid island structures may be oriented at an angle with respect to the average flow direction of the fluid, the average flow direction of the particles, or the long axis of the region for altering the particle concentration. The shapes of the channel segments are not limited to the approximately rectangular shapes shown in FIGS. 1-4. The channel segments may include curves or substantial changes in width. In cross-section, the channels described in FIGS. 1-4 may be square, rectangular, trapezoidal, or rounded. Other shapes for the channel cross-sections are also possible. The channel depth may be uniform across the region for altering the particle concentration, or the channel depth may vary laterally or longitudinally. Additionally, though FIGS. 1-4 show the microfluidic channels as approximately rectilinear pathways, the channels may be configured in other different arrangements. For example, in some implementations, the microfluidic channels may be formed to have a spiral configuration. For instance, the first microfluidic channel and the second microfluidic channel may be arranged in a spiral configuration, in which the first and second microfluidic channel are still be separated by the array of island structures, but where the longitudinal direction of fluid flow through the channels would follow a generally spiral pathway.

In some implementations, the microfluidic devices can be designed to incorporate redundancy so as to prevent particles that unintentionally pass with fluid through openings in a first array of island structures from ultimately being collected with the filtered fluid. For example, in some cases, the devices may be designed to include two or more "confinement channels" operating in parallel, i.e., two or more channels, such as channel 108 in FIG. 1, that are designed to impart repulsive forces to substantially prevent particles from passing through openings in the island array. Since particles would need to overcome the repulsive forces associated with each additional channel, the probability of a particle escaping with fluid that passes through openings between islands decreases as more confinement channels are added.

In some implementations, the devices described herein may be used in conjunction with other microfluidic modules for manipulating fluids and/or particles including, for example, filters for filtering sub-populations of particles of certain sizes. In addition, the devices described herein may be used in series and/or in parallel within a microfluidic system.

Altering Particle Concentration/Reducing Fluid Volume Using Inertial Focusing and Fluid Shifting Altering the concentration of particles within microfluidic samples is not limited to techniques that rely on a combination of fluid shifting with inertial lift forces and/or bumping forces to direct particles across fluid streamlines. Other internal forces, such as inertial focusing or viscoelastic focusing may be used in combination with fluid shifting as well.

With respect to inertial focusing, an inherent advantage is that the fluid forces depend on higher speed flows rather than low Reynolds number operation, thus leading to higher throughput, which is otherwise a common limitation of microfluidic devices.

Inertial focusing uses inertial forces to enable the precise lateral positioning of particles within a microfluidic channel, e.g., along a common streamline. Inertial focusing is based upon the notion that laminar flow of a fluid through microfluidic channels can result in the continuous and accurate self-ordering of particles suspended within the fluid from a randomly distributed state. In general, sorting, ordering, and focusing of particles in an inertial focusing system depends, inter alia, on the geometry of the microfluidic channel, the ratio of particle size to hydrodynamic cross-sectional size of the channel, and the speed of the fluid flow. Various channel geometries may require a predetermined particle-to-volume ratio of the particle to be focused to achieve a desired inter-particle spacing and thereby maintain ordering and focusing of those particles.

In general, a maximum particle-to-volume ratio for a specified particle size and channel geometry for inertial focusing alone can be determined using the formula:

$$MaxVolumeFraction = \frac{2N\pi a^2}{3hw}$$

where N is the number of focusing positions in a channel, a is the average focused particle diameter, h is the microfluidic channel height, and w is the channel width. Higher ratios may be achieved when additional forces are applied to the particles.

Different microfluidic channel geometries can be used to achieve inertial focusing of particles. For example, the microfluidic channel can be a symmetrically curved channel, such as S-shaped, sinusoidal, or sigmoidal. The channel can have various cross-sections, such as a rectangular, elliptical, or circular cross-section. Alternatively, the channel can be an asymmetrically curved channel having various shapes, cross-sections, and configurations as needed for a particular application (e.g., each curve in the channel can be a different size, or, for example, the odd-numbered curves in a channel may be a first size and shape and the even-numbered curves may be a second size and shape, or vice versa). For example, the channel can generally have the shape of a wave having large and small turns, where a radius of curvature can change after each inflection point of the wave. The maximum particle-to-volume ratio can be adjusted as necessary for the particular geometry.

The channel can be configured to focus particles within a fluid sample into one or more discrete streamlines at one or more equilibrium positions within the channel. In general, separation, ordering, and focusing are primarily controlled by a ratio of particle size to channel size and the flow characteristics of the system, but is independent of particle density. For example, analytes can have a hydrodynamic size that is in the range of about 1000 microns to about 0.01 microns. More particularly, analytes can have a hydrodynamic size that is in the range of about 500 microns to about 0.1 micron, such as between about 100 microns and about 1 micron. In general, the analyte size is limited by channel geometry. Analytes that are both larger and smaller than the above-described ranges can be ordered and focused within inertial focusing regions having laminar flow conditions.

Lateral migration of particles in shear flow arises from the presence of inertial lift, attributed mainly to the shear-gradient-induced inertia (lift in an unbounded parabolic flow) that is directed down the shear gradient toward the wall, and the wall induced inertia which pushes particles away from the wall. Particles suspended in fluids are subjected to drag and lift forces that scale independently with the fluid dynamic parameters of the system. Two dimensionless Reynolds numbers can be defined to describe the flow of particles in closed channel systems: the channel Reynolds number ($R_c$), which describes the unperturbed channel flow, and the particle Reynolds number ($R_p$), which includes parameters describing both the particle and the channel through which it is translating:

$$R_c = \frac{U_m D_h}{v}$$

and $$R_p = R_c \frac{a^2}{D_h^2} = \frac{U_m a^2}{v D_h}.$$

Both dimensionless groups depend on the maximum channel velocity, $U_m$, the kinematic viscosity of the fluid, and $v = \mu/\rho$ ($\mu$ and $\rho$ being the dynamic viscosity and density of the fluid, respectively), and $D_h$, the hydraulic diameter, defined as $2whl(w+h)$ (w and h being the width and height of the channel, respectively, for a channel having a rectangular or square cross-section). The particle Reynolds number has an additional dependence on the particle diameter $\alpha$. The definition of Reynolds number based on the mean channel velocity can be related to $R_c$ by $R_e = 2/3 R_c$. Inertial lift forces dominate particle behavior when the particle Reynolds number, $R_p$, is of order 1. Typically, particle flow in microscale channels is dominated by viscous interactions with $R_p \ll 1$. In these systems, particles are accelerated to the local fluid velocity because of viscous drag of the fluid over the particle surface. Dilute suspensions of neutrally buoyant particles are not observed to migrate across streamlines, resulting in the same distribution seen at the inlet, along the length, and at the outlet of a channel. As $R_p$, increases, migration across streamlines occurs in macro scale systems. An example of $R_p$, that allows localization of a flux of cells from a blood sample within a rectangular or square channel is about 2.9, but this can range from about 0.02 to 2.9 or higher. Again, different microfluidic channel geometries can be used to achieve inertial focusing of particles, resulting in corresponding Reynolds numbers suitable for those channel geometries. Examples and further discussion of inertial focusing can be found, for example, in U.S. Pat. No. 8,186,913, which is incorporated herein by reference in its entirety.

Generally, inertial focusing is used to focus particles to one or more equilibrium positions and then flow the different focused streams of particles to distinct outputs, where the particles are then collected. However, by adding the repetitive removal of fluid from the focused stream, the ability of inertial focusing to substantially increase particle concentration within a fluid (and/or reduce the concentration of particles in a fluid sample) may be greatly improved. In particular, the technique relies on two different behaviors that enable a substantial and rapid reduction in fluid volume: 1) a fast depletion of the near wall regions and 2) a reduced shear gradient lift driven migration of particles to their equilibrium positions.

Figure 5:
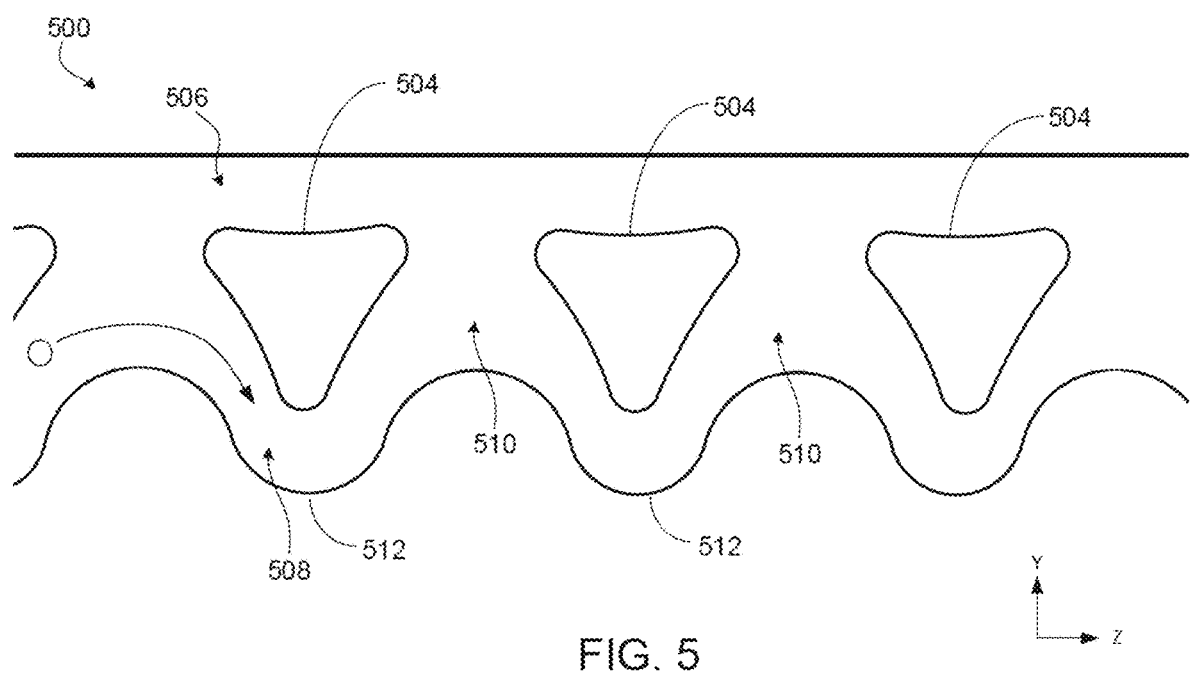
FIG. 5 is a schematic illustrating a top view of an example of a particle shifting area of a microfluidic device that relies on inertial focusing and fluid extraction

FIG. 5 is a schematic illustrating a top view of an example of a particle shifting area 500 of a microfluidic device, in which the particle shifting area 500 relies on inertial focusing in combination with repeated fluid extraction to enhance volume reduction from a particle-rich fluid sample. Fluid samples may be provided to particle shifting area 500 using, e.g., pumps, in a manner similar to that described with respect to other embodiments disclosed herein. The particle shifting area 500 includes an array of island structures 504 separating an elongated second fluid flow region 506 from an elongated first fluid flow region 508. The first fluid flow region 508 may also be called the "focusing channel" and the second fluid flow region 506 may be called the "particle-free channel." In the present example a particle containing fluid sample is introduced into flow region 508, whereas, a particle-free fluid sample, which may be the same or different fluid as that propagating in region 508, is introduced into flow region 506.

Each island 504 is separated from an adjacent island 504 in the array by a corresponding gap 510 that allows fluid to cross between the second and first flow regions. In contrast to the devices shown in FIGS. 1-4, the first flow region 508 has an undulating channel wall 512 (e.g., approximately sinusoidal in shape) in which the channel width (along the y-direction in FIG. 5) alternates between being narrow and enlarged along the longitudinal direction (along the z-direction in FIG. 5). Additionally, each island structure 504 has a curved contour that follows the curvature of portions of the peaks and troughs in the channel wall 512. That is, a side of each island and an opposing side of the second channel have substantially matching contours. In the present example, this leads to flow region 508 having an undulating longitudinal pathway through which the particle-carrying fluid sample propagates.

More specifically, a first turn through flow region 508 is narrow and the matching contours of the wall 512 and island 504 have small radii of curvature, whereas a second adjacent turn through flow region 508 is wider and the matching contours of the wall 512 and island have larger radii of curvature. This pattern of a relatively small radius of curvature followed by a relatively larger radius of curvature is repeated over the length of the flow region 508. Thus, the microfluidic channel is asymmetrically curved to create higher fluid speeds closer to the wall 512 than away from the wall 512. Depending on the flow rate of a particle carrying fluid, the fluid pathway curvature of the first flow region 508 may generate inertial forces that focus and retain particles 502 along one or more fluid streamlines within the first flow region 508.

Additionally, the fluidic resistance near the gaps 510 between islands 504 decreases so that a portion of fluid tends to follow the low resistance path and shift/flow into the second flow region 506. This fluid flow also tends to pull particles 502 traveling with fluid in the direction of the gaps 510. However, in certain implementations, the inertial forces generated by the undulating fluid pathway of this region are great enough to shift the particle 502 across fluid streamlines and away from the gaps 510 so that the particle 502 remains suspended in the portion of fluid traveling through the first flow region 508. The second fluid flow region 506 can be configured to have a width that progressively increases so the fluidic resistance in that region decreases over the channel length. As a result, greater amounts of particle-free fluid will shift into the second fluid flow region farther downstream along the channel, and lead to an increase in particle concentration in the first fluid flow region 508.

Figure 6A:
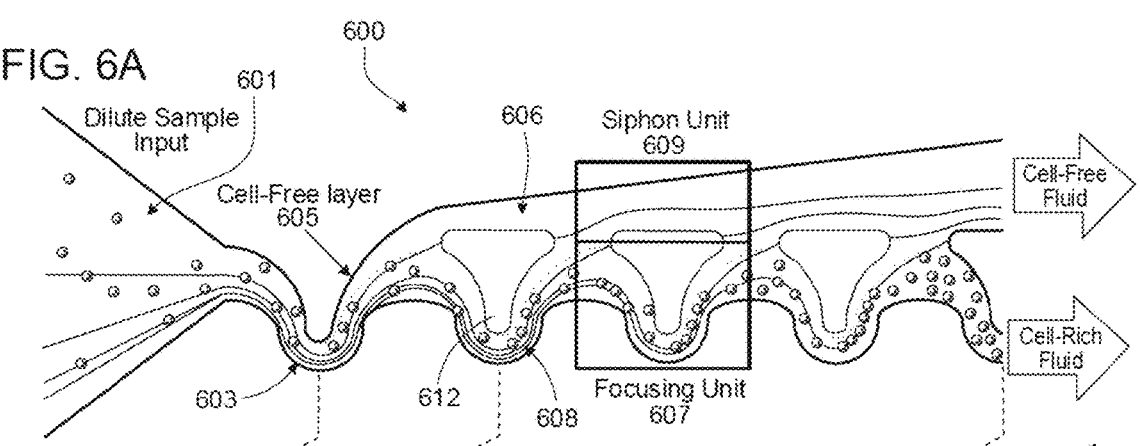
FIG. 6A is a schematic depicting how fluid streamlines may behave within a microfluidic device that combines inertial focusing with repeated fluid extraction.

FIG. 6A is a schematic depicting how fluid streamlines may behave within a microfluidic device 600 that combines inertial focusing with repeated fluid extraction. The structure of the device shown in FIG. 6A is similar to the device 500 and includes an input region 601, where a fluid suspension containing a dilute concentration of particles (e.g., cells) is introduced. As the dilute sample of particles enters the device, the fluid sample is accelerated when the microfluidic channel converges toward a first narrow neck region 603. A particle-free layer (labeled "cell free layer" in FIG. 6) 605 forms after the fluid sample passes through the neck region 603 as a result of the cells moving away from the wall by Dean flow. A portion of this particle-free layer 605 then passes/is siphoned off toward the second fluid flow region 606 at the first island structure 612, whereas the particles remain in the first fluid flow region 608. The amount of the fluid sample that passes into the second fluid flow region 606 depends on the hydraulic resistance of the openings and the second fluid flow region 606 relative to the hydraulic resistance of the first fluid flow region 608. The process of accelerating the particle-rich fluid to create a particle-free layer, and passing the particle-free layer into the second fluid flow region 606 is repeated multiple times at each island 612 until the end of the device where the separate flows may be captured for further processing or removal from the device. For instance, the device 600 may be understood as having a repeating array of focusing units and siphoning units arranged in parallel (i.e., a "focusing-siphoning unit pair"). An example of the regions corresponding to a single focusing unit 607 and a single siphoning unit 609 are depicted in FIG. 6A. The focusing unit 607 includes the area adjacent to an island structure 612 where the walls of the microfluidic channel have relatively high curvature to induce inertial focusing. The siphoning unit 609 includes the area adjacent to the same island structure, but opposite to that of the focusing unit 607, that has relatively less curvature and which provides a wider pathway for fluid to travel, resulting in a lower hydraulic resistance. In the example shown in FIG. 6, the width of each siphoning unit 609 (as determined along a direction transverse to fluid flow) increases along the direction of fluid flow, leading to lower fluidic resistance and therefore an increase in the amount of fluid passing from the first fluid flow region 608.

Figure 6B:
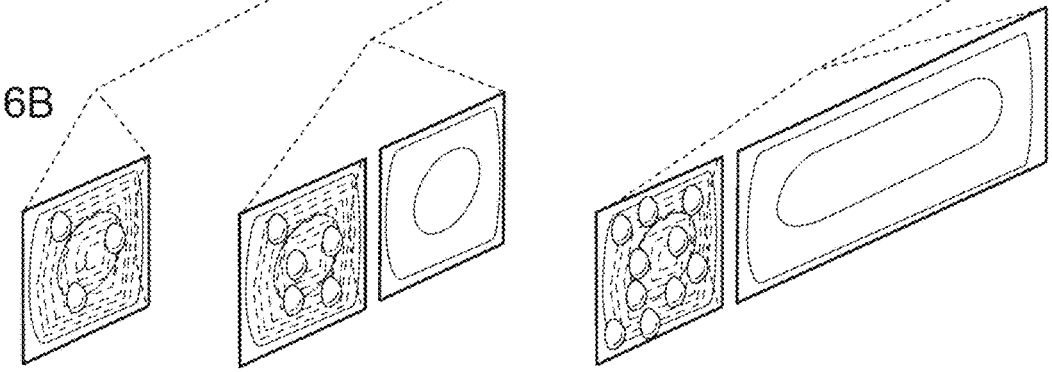
FIG. 6B includes plots of simulated fluid flow for different cross-sections of the device shown in FIG. 6A.

FIG. 6B includes plots of simulated fluid flow for different cross-sections of the device 600 shown in FIG. 6A. The plots in FIG. 6B depict the Dean flow vectors and velocity profile which causes the formation of the cell free layer. As can be seen from these plots, the overall flow speed, and thus the inertial force, of the fluid sample decreases along the length of the microfluidic channel as fluid passes into the second fluid flow region 606. In other words, to achieve a given level of volume reduction, the flow speed must be reduced to a fixed degree, independent of the number of units used.

An important design consideration for a device that combines inertial focusing with repeated fluid extraction is the percentage of the fluid that is siphoned at each siphoning unit. Ideally, the greater the amount of particle-free fluid that is removed at each siphoning unit, the quicker one will be able to obtain a desired particle concentration in the particle-rich fluid. However, it is also the case that the higher the percentage of fluid that is siphoned, the greater is the risk that particles will be carried away with the siphoned fluid if the inertial forces do not shift the cells out of the larger siphoned fluid fraction.

Figure 7:
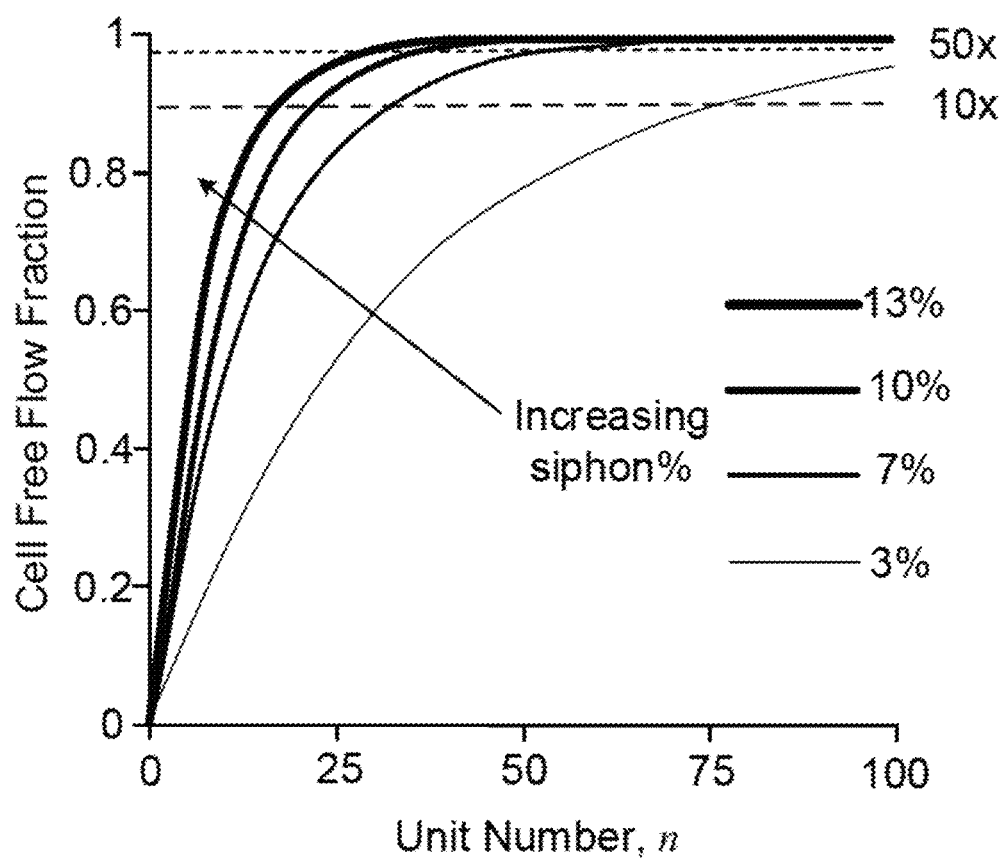
FIG. 7 is a plot that depicts the cell free flow fraction as function of the number of siphon-focusing unit pairs for the device structure shown in FIG. 6B

FIG. 7 is a plot that depicts the results of a calculation based on the device structure shown in FIG. 6B. The calculation was performed to determine the Cell Free Flow Fraction as a function of the number of siphon-focusing unit pairs and the percentage of fluid that passes into the particle-free layer at each opening between the island structures of the device. "Cell Free Flow Fraction" refers to the fraction of all fluid that has been siphoned out. For example, if the siphon percentage is 10%, then after one unit the cell free flow fraction is 10%. The other 90% remains in focusing units. Then, in the second unit remove 10% of the remaining 90% is removed (i.e., 9% of the overall fluid). Thus, after two units the Cell Free Flow Fraction is 19%. This continues on. The plot also includes two horizontal dashed lines, with the top line representing a factor of 50 times reduction in fluid volume of the particle-rich fluid, and the bottom dashed line representing a factor of 10 times reduction in fluid volume of the particle-rich fluid. The four different curves in FIG. 7 represent siphoning at four different percentages, with the smallest siphon percentage corresponding to the bottom curve and the highest siphon percentage corresponding to the top curve in the plot. As shown in FIG. 7, higher siphon percentages (i.e., the percentage of fluid siphoned at each siphon unit) decrease the overall number of units required to reach an equivalent volume reduction factor seen at the intersections of the 10× and 50× dashed lines.

A microfluidic device that combines inertial focusing and siphoning is not limited to the configuration shown in FIG. 5. For example, in some implementations, a combined inertial focusing and siphoning device may have a configuration that includes an second fluid flow channel, a first (center) fluid flow channel and a third fluid flow channel similar to the device shown in FIG. 2, with the exception that the device would be constructed to induce inertial focusing in the center channel. For example, the center channel may be configured to have an undulating pathway/shape in which the channel width (as determined transverse to the direction of fluid flow) alternates between narrow and enlarged. This may be achieved by constructing each of the first and second array of island structures to have matching contours that alternate between regions of high and low curvature. As in the example of FIG. 2, fluid passes into the second and third channels at the openings/gaps between the island structures. Alternatively, in some implementations, the device can be constructed to induce inertial focusing in the second and third fluid flow channels. For example, each of the second and third fluid flow channels may be configured to have an undulating pathway/shape in which their widths alternate between narrow and enlarged. This may be achieved by constructing the walls of the second channel and the opposing array of island structures to have matching contours that alternate between regions of high and low curvature, whereas the walls of the third channel and an opposing array of island structures may also have matching contours that alternate between regions of high and low curvature. At the gaps/openings between the island structures in each array, fluid may pass from the second channel into the center channel and from the third channel into the center channel.

In some implementations, the combined inertial focusing and siphoning device may have two fluid inputs, similar to the device 400 shown in FIG. 4, so that the device acts as a fluid exchanger, where particles are transferred from a first fluid to a second fluid. That is, a first fluid sample may be introduced through input 406, whereas a second different fluid sample containing particles 402 may be introduced into input 404. Initially, a portion of the second fluid sample containing the particles 402 and first fluid sample propagate side by side through channel 410. The walls of the first channel 410 and the island structures 412 may be configured so that the first channel 410 has an undulating pathway/shape in which the width of the channel alternates between narrow and enlarged (similar to the configuration shown in FIG. 5). The undulating channel 410 leads to focusing of the particles along streamlines within the first fluid sample in channel 410. Simultaneously, portions of the second fluid sample that are free of particles 402 are extracted from channel 410 at the gaps 414 between islands 412 into the second channel 408. After repeated extraction of the second fluid sample, the particles 402 eventually are entirely transferred to the first fluid sample within channel 410, and the second fluid sample is particle free.

In some implementations, a microfluidic device includes a particle shifting area having multiple channels that rely on inertial focusing in combination with repeated fluid extraction. Using multiple channels allows, in some implementations, a substantial increase in the throughput of a microfluidic device. For example, multiple copies of the particle shifting area 500 shown in FIG. 5 may be arranged in parallel. The output of each of the channels containing the particles may be delivered to a common repository. Similarly, the output of each of the channels containing the particle-free fluid also may be delivered to a different common repository.

In contrast to conventional centrifugation, an advantage of devices that use the combined inertial focusing and siphoning techniques is that particles are exposed to heightened forces for a shorter duration (e.g., fractions of seconds) than during centrifugation (e.g., several minutes). Additionally, compaction of particles does not occur in the microfluidic volume reduction process. Cell compaction, which may occur in centrifugation processes, is known to mechanically damage certain cells as well as alter gene expression (see, e.g., Peterson, B. W., Sharma, P. K., Van Der Mei, H. C. & Busscher, H. J. "Bacterial Cell Surface Damage Due to Centrifugal Compaction," Applied and Environmental Microbiology 78, 120-125 (2012), incorporated herein by reference in its entirety). Additionally, the short duration over which cells may be exposed to heightened forces in a combined siphoning and inertial focusing device results in little or no restructuring of cells' interiors. In contrast, centrifugation techniques are susceptible to causing the dislocation of organelles. Moreover, there is no need for sterile breaks between steps in the combined siphoning and inertial focusing devices, unlike when transferring samples from a centrifuge. Thus, compared to centrifugation, the combined siphoning and inertial focusing devices offer a more efficient closed system for performing common biomedical tasks.

Increasing Particle Concentration/Reducing Fluid Volume Using Viscoelastic Focusing As explained above, viscoelastic focusing also may be used in combination with fluid shifting to alter the concentration of particles within a fluid sample. In some implementations, viscoelastic focusing includes the addition of specified concentrations (e.g., micromolar concentrations or other concentrations) of one or more drag-reducing polymers (e.g., hyaluronic acid (HA)) to a fluid that results in a fluid viscoelasticity that can be used to control the focal position of the particles within the moving fluid at different Reynolds numbers ($R_e$).

With viscoelastic focusing, the volumetric flow rate at which a particle-carrying fluid is driven results in the formation of a localized streamline in the fluid at or near a center of the channel. The localized streamline defines a width that is substantially equal to or slightly greater than a hydraulic diameter of a particle within the fluid. By adding the drag-reducing polymer to a Newtonian fluid (e.g., water or a physiological saline solution), the particle in the fluid is focused into the localized streamline, creating particle-free regions at the edges of the channel (e.g., the regions closest to the channel boundaries or walls).

Thus, similar to inertial focusing, viscoelastic focusing enables the precise positioning of particles within a fluid along a common streamline. In contrast to inertial focusing, viscoelastic focusing has an equilibrium position at the center of the channel cross-section, i.e., along a longitudinal path extending in a direction of fluid flow and centered between walls of the channel. Viscoelastic focusing also works across large ranges of flow rates and Reynolds numbers. The technique of viscoelastic focusing thus can be coupled with fluid extraction as described herein (e.g., repetitive removal/siphoning of fluid from the focused stream) to substantially alter particle concentration within a fluid.

Any of the devices described herein may be used with viscoelastic focusing to focus particles to a streamline within a fluid and alter the particles' concentration within the fluid. For example, viscoelastic focusing may be used with the device 200 shown in FIG. 2. A pump (not shown) connected to the inlet of channels 206 and 210 may be operated to drive a fluid that carries suspended particles 202. In some implementations, the pump is operated to drive the fluid through the channels at volumetric flow rates that result in the formation of a localized streamline in the fluid at or near a center of the center channel 208, e.g., defined by the axis 220. The localized streamline 220 defines a width that is substantially equal to or greater than a hydraulic diameter of the particle 202. The particles in the fluid are focused into the localized streamline 220. The localized streamline 220 represents a portion of the fluid into which the suspended particles 202 are focused. That is, the suspended particles are focused into a streamline formed by the fluid flow at or near a center of the channel 208. At the same time, fluid may be extracted at the gaps/openings between the islands 212, 214 that separate the second and third channels 206, 210 from the center channel 208. Because the particles are focused to a center streamline, the particles 202 are located further away from the gaps between islands and are less likely to be carried out of the center channel 208 with the portions of the fluid sample being extracted into the second and third channels 206, 210. That is, at each gap a portion of particle-free fluid is extracted from the center channel 208 into either channel 206 or channel 210, resulting in an increase in the concentration of particles within the center channel 208. After repeated siphoning of fluid at the gaps, the concentration of the particles may be increased, e.g., from 10 to 100 times or more.

The fluid in which the particles 202 are suspended and which is flowed through the channels 206, 208, 210 can include a Newtonian fluid, e.g., water or other Newtonian fluid, or a drag-reducing polymer mixed with a Newtonian fluid. In general, any polymer (or material) that can decrease a drag on particles, e.g., by exerting viscoelastic normal stresses on the particles, at the volumetric flow rates described herein can be implemented as an alternative or in addition to HA. In other words, any material (e.g., polymer, or other material) which, when mixed with a Newtonian fluid, alters a drag on a particle suspended in the fluid-material mixture, relative to a drag on the particle suspended in the Newtonian fluid without the material can be implemented as an alternative or in addition to HA. Such materials can include, e.g., polyethylene oxide (PEO), polyacrylamide, gelatin, to name a few. The particles can include rigid particles, e.g., beads, or deformable particles. In some implementations, the particles can include biological particles, e.g., cells. The drag-reducing polymer can include hyaluronic acid (HA). The molecular weight of HA can be between 350 kDa and 1650 kDa. The Reynolds number of the fluid flow can be between 0.001 and 4500, e.g., between 0.01 and 20, between 0.01 and 15, between 0.01 and 10, between 0.01 and 1, between 0.1 and 1000, between 0.1 and 100, between 0.1 and 20, between 0.1 and 10, between 0.1 and 1, between 1 and 1000, between 1 and 100, or between 1 and 20. The concentration of the drag-reducing polymer can be between about 0.001-1% g/mL (0.00001-0.01 g/mL) such as between about 0.01-0.1% g/mL (0.0001-0.001 g/mL). Further discussion of viscoelastic focusing can be found, e.g., in WO 2015/116990, which is incorporated herein by reference in its entirety.

Microfluidic Device Design Parameters

Figure 16:
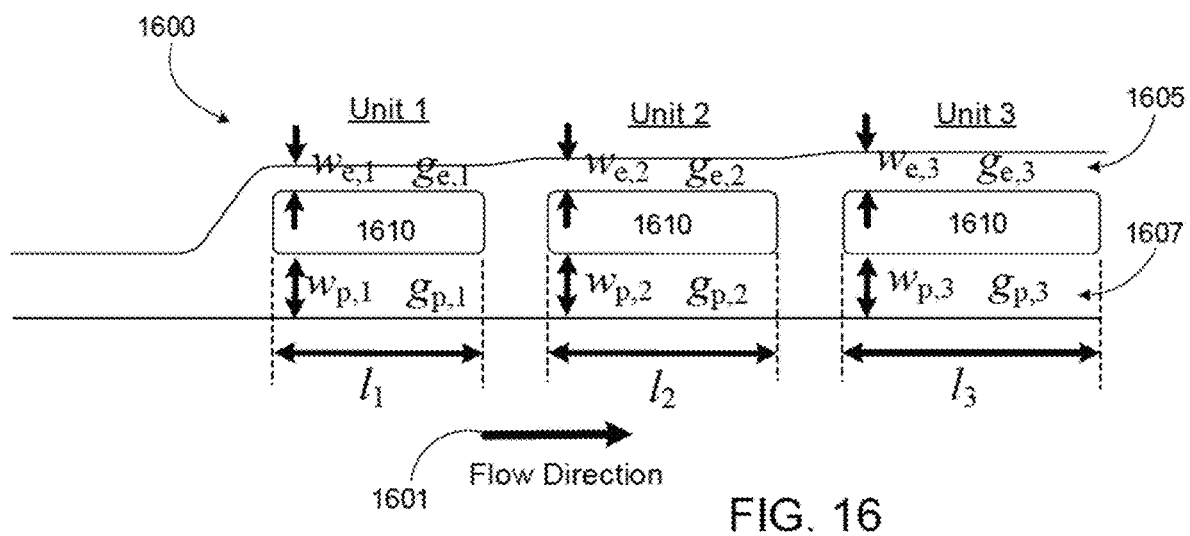
FIG. 16 is a schematic illustrating a top view of an example particle and fluid shifting area of a microfluidic device.

The effect of various design parameters on the operation of the microfluidic device will now be described. For reference, FIG. 16 is a schematic illustrating a top view of an example particle and fluid shifting region 1600 containing a row of island structures 1610. The row of island structures 1610 separates an "extraction" microfluidic channel 1605 from a "particle" microfluidic channel 1607. The primary direction of fluid flow is indicated by the arrow 1601. The width of the extraction channel 1605 (defined along the y-direction) expands along the length of the channel, whereas the width of the particle channel 1607 (defined along the y-direction) remains essentially constant along the length of the channel. During operation of the device, fluid is extracted into the extraction channel 1605 through the openings between the islands 1610, while particles traveling within the particle channel 1607 are retained in the particle channel 1607 by repulsive forces, e.g., inertial lift forces. For the purposes of the following discussion, the channels and islands may be understood as being arranged into separate "units" (see Unit 1, Unit 2 and Unit 3 in FIG. 16). Specifically, FIG. 16 illustrates three units of an array with each unit including a portion of the exterior microfluidic channel 1605, an island 1610, and a portion of the particle channel 1607.

The relevant design parameters for the particle and fluid shifting region 1600 include the length of each unit, the width of each channel, and the fluid shift for each unit. The fluid shift, $f_s$, is the fraction of the fluid flow, q, that shifts between channels at each unit (i.e., at the openings between the island structures). Together these parameters determine the fluid conductance of the channels in each unit of the device. Thus, each unit has a particle channel with length $l_i$, a particle channel width $w_{p,i}$, and a particle channel fluidic conductance $g_{p,i}$, where i refers to the unit number. Each unit also has an extraction fluid channel with length $l_i$, an extraction channel width $w_{e,i}$, and an extraction channel fluidic conductance $g_{e,i}$, where i refers to the unit number. In the example described here, all channels are rectangular in shape and the fluid shift is the same for each unit. The basic method presented here can be easily modified for non-rectangular (e.g., curving) channels and varying shift.

At each unit, the total flow divides between the particle and extraction fluid channels in proportion to their relative fluidic conductances. Thus, the fraction of the total flow that flows through the particle channel 1607 in the $i^{th}$ unit is $$f_{p,i} = \frac{q_{p,i}}{q_{p,i} + q_{e,i}} = \frac{g_{p,i}}{g_{p,i} + g_{e,i}}$$

where $q_{p,i}$ and $q_{e,i}$ are the flow rates of the particle and extraction fluid channels, respectively. Similarly, the fraction of the total flow that flows through the extraction fluid channel 1605 in the $i^{th}$ unit is $$f_{e,i} = \frac{q_{e,i}}{q_{p,i} + q_{e,i}} = \frac{g_{e,i}}{g_{p,i} + g_{e,i}}$$

The dimensions of the particle channel 1607 are chosen to optimally shift particles across streamlines (e.g., away from the extraction fluid channel 1605). Because the flow rate $q_{p,i}$ changes along the length of the device, the particle channel dimensions may be altered to maintain optimal particle shifting. For example, as $q_{p,i}$ decreases, the unit length $l_i$ may be increased to compensate for the weakening inertial lift force operating on particles.

The dimensions of the extraction fluid channel 1605 are chosen to provide a conductance $g_{e,i}$ such that a precise fraction of the fluid in the particle channel 1607 shifts to the extracted fluid channel at each unit. This fractional amount is called the fluid shift, $f_s$. The result of this shifting is that the fraction of flow in the particle channel decreases by a fixed factor at each unit:

$$f_{p,i} = (1 - f_s) f_{p,i-1}$$

For example, if $f_s$=0.1, then fraction of flow in the particle channel will be 90% of the fraction of flow in the particle channel of the previous unit. More generally, because $f_{p,0}$=1, $$f_{p,i} = (1 - f_s)^i$$

Thus, for the example case shown in FIG. 16 in which the particle and fluid shifting region is divided into three units, $f_s$=0.1, $f_{p,1}$=0.9, $f_{p,2}$=0.81, and $f_{p,3}$=0.729.

Recall that the fraction of flow in the particle channel is also described by $$f_{p,i} = \frac{g_{p,i}}{g_{p,i} + g_{e,i}}$$

Substituting for $f_{p,i}$ and solving for $g_{e,i}$:

$$g_{e,i} = ((1 - f_s)^{-i} - 1) g_{p,i}$$

Thus, for each unit the conductance of the extracted fluid channel can be written in terms of the conductance of the particle channel and the fluid shift. The fluidic conductance, g, of each channel is a function of its dimensions and the fluid viscosity. In the device described here, each channel is rectangular and therefore has conductance that can be expressed as $$g \approx \left(\frac{h^4}{12 \eta l \alpha}\right)(1 - 0.63\alpha)$$

Here, $\eta$ fluid viscosity, l is channel length, w is channel width, h is channel height, and $\alpha$=h/w. A more accurate infinite series-based formula is also available (Tanyeri et al., "A microfluidic-based hydrodynamic trap: Design and implementation (Supplementary Material)." *Lab on a Chip* (2011).) Computational modeling or empirical methods can be used to determine the conductance of more complex channel geometries. (Note that in this description it is simpler to focus on fluidic conductance, g, rather than fluidic resistance, R. The two quantities are simply related by g=1/R.)

Using the above formulas, a microfluidic device for increasing the concentration of particles within a fluid sample may be implemented as follows:
1. The dimensions of the particle channel are chosen for each unit in the device. As mentioned, the dimensions are chosen to optimally shift particles away from the extracted fluid channel.
2. Using these dimensions and the fluid viscosity, the particle channel conductance $g_{p,i}$ is determined for each unit using the rectangular channel conductance formula (or an equivalent method).
3. The extraction fluid channel conductance $g_{e,i}$ is then evaluated for each unit using the previously determined $g_{p,i}$ and $f_s$. The width of the extraction fluid channel, $w_{e,i}$, is then chosen to give the desired $g_{e,i}$ for each unit. In practice, the width may be determined by evaluating fluidic conductance (using the above formula) across a wide range of channel widths and then interpolating to find the channel width that gives the desired channel conductance.

For concentrators with straight channels that rely on inertial lift forces to shift particles across streamlines, the following are device design and operation guidelines:

First, as described in "Inertial Microfluidics," Di Carlo, Lab Chip (9), 3038-3046, 2009 (incorporated herein by reference in its entirety), the ratio of the lateral (across channel) particle velocity $U_y$ to the longitudinal (in direction of fluid flow) velocity $U_z$ is proportional to the particle Reynolds number $R_p$:

$$\frac{U_y}{U_z} \propto R_p = \frac{U_m a^2}{\nu D_h}$$

Here $U_m$ is the maximum channel velocity, a is the particle diameter, $\nu$ is the kinematic viscosity of the fluid, and $D_h$ is the hydraulic diameter of the channel. (For channels of rectangular cross-section with width w and height h, $D_h=(2wh)/(w+h)$.) Because it is the aim of the particle concentrator device described here to use inertial lift forces to efficiently move particles across streamlines (e.g., maximize $U_y/U_z$), it is recommended that the channel dimensions and flow conditions be selected so as to maximize particle Reynolds number $R_p$ in the particle channel to the extent permitted by other practical constraints, such as operating pressure. Throughout the device, the particle Reynolds number $R_p$ in the particle channel should ideally be greater than about 0.01, though it may be much larger than this, possibly greater than 100.

For a given particle diameter $\alpha$ and kinematic viscosity $v$, a target particle Reynolds number $R_p$ can be achieved through many different combinations of channel dimensions and channel velocities. One strategy for increasing $R_p$ would be to select a very small (relative to a) hydraulic diameter $D_h$. However, channel resistance has a quartic dependence on $D_h$, and choosing an unnecessarily small $D_h$ comes at the cost of highly increased operating pressure. On the contrary, the operating pressure scales linearly with channel velocity $U_m$, so a good alternative strategy is to design a device with a modest hydraulic diameter $D_h$ and then increase channel velocity $U_m$ (and therefore $R_p$) at the time of operation as needed to achieve high yield of particles. For a channel with square cross-section, such that $D_h=w=h$, a value of $D_h$ approximately five times the particle diameter a is a reasonable choice: $D_h=5\alpha$.

Second, the length of the openings (in the longitudinal direction) between islands should be greater than about $\alpha$ and less than or equal to about w. If the length of the opening is less than $\alpha$, the opening may clog with particles, thereby disrupting flow through the opening. An opening with length approximately equal to w is unlikely to clog with particles and provides adequate room for fluid to cross between islands to the adjacent channel. An opening with a length greater than w will work but provides no particular benefit and comes at the cost of wasted space.

Third, the length of the islands l should be greater than or equal to the length of the openings between islands. As aforementioned, it is the aim of the particle concentrator device to use inertial lift forces to efficiently move particles across streamlines. Because particles only experience inertial lift forces as they travel alongside islands, particles should travel most of their longitudinal distance alongside islands, rather than across openings between islands. Put another way, if the length of islands and the length of the openings between islands are equal, then particles experience inertial lift forces along just 50% of the distance they travel. On the other hand, if the length of the islands is four times the length of the openings, then particles experience inertial lift forces along 80% of the distance they travel.

A loose upper limit on the length of islands l is the length required for particles to migrate to equilibrium focusing positions. Any additional channel length beyond what is required for particles to reach equilibrium does not contribute to shifting particles across streamlines. A formula for the channel length $L_f$ required for particles to reach equilibrium is given in "Inertial Microfluidics," Di Carlo, Lab Chip (9), 3038-3046, 2009:

$$L_f = \frac{\pi \mu w^2}{\rho U_m a^2 f_L}$$

Here $\mu$ is dynamic viscosity, w is channel width, $\rho$ is fluid density, $U_m$ is the maximum channel velocity, $\alpha$ is the particle diameter, and $f_L$ is a dimensionless constant ranging from about 0.02 to 0.05 for channels with aspect ratios (h/w) ranging from about 2 to 0.5. While $L_f$ provides an upper bound, it is a loose upper bound and exceeds the optimal length of islands l. This is because the lift force on particles is very strong near the channel wall (proportional to $\alpha^6$), but falls off sharply with distance from the wall (proportional to $\alpha^3$ near the center of the channel). Thus, a concentrator device will more efficiently shift particles across streamlines if the particles are kept near the channel wall by using an island length l that is significantly less than $L_f$.

Given these considerations, a reasonable intermediate value for the island length is about l=4w. This is an approximate value and necessarily depends on the values selected for other parameters, such as the fluid shift $f_s$. It is also important to note that the length of the islands l need not be constant along the length of the device. Rather, as the maximum channel velocity $U_m$ and particle Reynolds number $R_p$ in the particle channel decrease, the lengths of the islands can be increased to compensate. For example, a factor of two decrease in $R_p$ can be compensated by a factor of two increase in island length l. Up to a point, the lateral deflection distance of particles per unit is expected to be roughly proportional to the island length l.

Fourth, the fluid shift $f_s$ should be greater than 0.2% and ideally greater than 1.0%. If the fluid shift is small, e.g., 0.1%, then the total number of shifts (units) needed to achieve a significant volume reduction, e.g., 10×, is very large and the device itself must therefore be very long. Provided the maximum channel velocity $U_m$ is sufficiently high to place the particle Reynolds number $R_p$ in the prescribed range, an extremely small shift, e.g., 0.1%, should not be necessary. Depending on the maximum channel velocity $U_m$, a fluid shift $f_s$ in the range of about 1% to 5% should perform well for a device designed and operated as outlined here.

It is important to note that the fluid shift $f_s$, like the length of the islands l, need not be constant along the length of the device. Rather, as the maximum channel velocity $U_m$ and particle Reynolds number $R_p$ in the particle channel decrease, the fluid shift $f_s$ can be reduced to compensate. For example, a factor of two decrease in $R_p$ can be compensated by a factor of two decrease in fluid shift $f_s$. Either or both of these compensation strategies can be implemented to optimize device efficiency and performance.

For any given device design and particle size $\alpha$, the final parameter choice is the device operating flow rate, which directly determines the maximum channel velocity $U_m$ and the particle Reynolds number $R_p$ in the particle channel. For a device designed as outlined, there will be a minimum flow rate required for good performance. Below this threshold flow rate, the inertial lift forces will be insufficient to shift particles far enough from the island wall to avoid being shifted as fluid is extracted (siphoned), thus resulting in low yield of particles. While the formulas provided here enable one to make rough estimates of the threshold flow rate, the most accurate and relevant method of determining the threshold flow rate is empirically.

Other design and optimization strategies may also result in effective, high performance concentrator devices.

A microfluidic device that is configured to shift particles of a given size can, in some implementations, be scaled to effectively shift particles of a different size. For instance, for a device that employs inertial lift forces to shift particles across fluid streamlines, one can scale the dimensions of the particle shifting area with particle size and alter the flow conditions, so long as the value of the particle Reynolds number, $R_p$, is preserved. The particle Reynolds number can be expressed as:

$$R_p = \frac{U_m a^2}{\nu D_h}$$

where $U_m$ is the maximum channel velocity, $\alpha$ is the particle diameter, $\nu$ is the kinematic viscosity of the fluid, and $D_h$ is the hydraulic diameter of the channel. (For channels of rectangular cross-section with width w and height h, $D_h$= (2wh)/(w+h).) For example, consider a Shifting Area 1 that effectively shifts particles of size $\alpha$. One method of designing a Shifting Area 2 that effectively shifts particles of size $2\alpha$ is scale all dimensions of Shifting Area 1 by a factor of 2 (i.e., double the length, width, and height of all features). To maintain the same $R_p$ in Shifting Area 2, the maximum channel velocity $U_m$ must be decreased by a factor of 2.

Other methods of scaling the dimensions of particle shifting areas and flow conditions with particle size are also possible.

Ease of microfluidic device manufacturing is largely determined by the aspect ratio (height divided by width) of the device structures, with smaller aspect ratio devices being easier to manufacture at low cost and with high manufacturing yield. We can define the aspect ratio in two ways. The minimum aspect ratio is the structure height, h, divided by the minimum structure width, $w_{min}$. The overall aspect ratio is the structure height, h, divided by the diameter, D, of a circle with the same area as the structure. Here, $D=\sqrt{(4A/\pi)}$, where A is the area of the structure.

As an example, for a microfluidic device having substantially straight channels, the island structures may have a length of about 50-1000 µm, a width of about 50 µm, and a height of about 52 µm. With these dimensions, the minimum aspect ratio of the islands is 1.04, and the overall aspect ratio is in the range 0.92-0.21. The aspect ratio could be further reduced by increasing the width of the islands. In another example, for a microfluidic device having curved channels, the island structures may have an irregular shape with a $w_{min}$ in the range of about 42-80 µm, A in the range of about 18,000-61,000 µm², and a height of 52 µm. With these dimensions, the minimum aspect ratio of the islands is in the range 1.24-0.65, and the overall aspect ratio is in the range 0.34-0.19.

In both cases, the low aspect ratio of the structures enables straightforward fabrication of molded PDMS and epoxy devices, as well as injection molded plastic devices. This is a major advantage of this class of devices: they are not only extremely useful from a functional perspective, but they also are fundamentally scalable and economical from a commercial perspective.

Microfluidic Device Dimensions

For generally spherical particles being transported through a microfluidic device having at least two channels separated by an array of island structures, with gaps between adjacent islands (see, e.g., FIG. 1), the depth (e.g., as measured along the x-direction in FIG. 1) and width (e.g., as measure along the y-direction in FIG. 1) of each microfluidic channel is preferably in the range of about 2 times to about 50 times the diameter of a single particle. With respect to the rigid structures that form the gaps through which fluid is extracted, the width of the structures may be up to about 10 times the width of the a single microfluidic channel, whereas the length of the structures may be between about 0.25 times the channel width up to about 50 times the channel width.

As an example, for a generally spherical particle having a diameter of about 8 microns, a microfluidic device having two microfluidic channels separated by an array of rigid structures similar to the configuration shown in FIG. 1 may have the following parameters: each microfluidic channel may have a depth about 52 µm, each microfluidic channel may have a range of widths between about 10 µm to about 5000 µm, each island structure may have a width of about 50 µm, each island structure may have a length of about 200 µm.

Other examples of dimensions are set forth as follows.

For instance, the distance between the outer walls of the area containing the different fluid flow regions, i.e., as measured transverse to the fluid flow direction, can be configured to be between about 1 µm to about 100 mm (e.g., about 10 µm, about 50 µm, about 100 µm, about 500 µm, about 1 mm, about 5 mm, about 10 mm, or about 50 mm). Other sizes are possible as well. The width of each fluid flow region/channel (e.g., the width of second and first microfluidic channels 106 and 108 in FIG. 1), measured transverse to the fluid flow direction, can be configured to be between about 1 am to about 10 mm (e.g., about 50 µm, about 100 µm, about 250 µm, about 500 µm, about 750 µm, about 1 mm, or about 5 mm). Other distances are possible as well.

The length of the gaps/openings between the island structures, as measured along the fluid flow direction (e.g., along the z-direction in FIG. 1), can be configured to be between about 500 nm to about 1000 µm (e.g., about 1 µm, about 2 µm, about 5 µm, about 10 µm, about 50 µm, about 100 µm, about 200 µm, about 500 µm, or about 750 µm). In some implementations, the length of each successive opening is greater than or less than the length of the last opening. For example, in a channel configured to have a decreasing fluidic resistance along the fluid pathway, each successive opening may be larger so that a greater amount of fluid is extracted through the opening. The island structures that separate different fluid flow regions can be configured to have a maximum length between about 10 nm to about 10 µm, and a maximum width between about 10 nm to about 10 µm. Other dimensions for the gaps and island structures are possible as well.

The height of the fluid flow regions and the island structures within the particle shifting area (e.g., as measured along the x-direction in FIG. 1) are within the range of approximately 100 nm to approximately 10 mm. For example, the height of the channel can be about 500 nm, about 1 µm, about 5 µm, about 10 µm, about 50 µm, about 100 µm, about 500 µm, about 750 µm, about 1 mm, or about 5 mm. Other heights are possible as well. The microfluidic flow regions can have a cross-sectional area that falls, e.g., within the range of about 1 µm² to about 100 mm².

Microfluidic Systems

In some implementations, the particle shifting areas of the microfluidic devices described herein are part of a larger, optional, microfluidic system having a network of microfluidic channels. Such microfluidic systems can be used to facilitate control, manipulation (e.g., separation, segregation, mixing, focusing, concentration), and isolation of liquids and/or particles from a complex parent specimen. During the isolation process, microfluidic elements provide vital functions, for example, handling of biological fluids or reproducible mixing of particles with samples.

For example, the microfluidic system may include additional areas for separating particles according to size and/or shape using other techniques different from inertial lift forces. These other techniques include, for example, deterministic lateral displacement. These additional areas may employ an array of a network of gaps, in which a fluid passing through a gap is divided unequally into subsequent gaps. The array includes a network of gaps arranged such that fluid passing through a gap is divided unequally, even though the gaps may be identical in dimensions. In contrast to the techniques described herein for separating particles based on a combination of inertial lift forces and fluid extraction, deterministic lateral displacement relies on bumping that occurs when the particle comes into direct contact with posts forming the gaps. The flow of the fluid is aligned at a small angle (flow angle) with respect to a line-of-sight of the array. Particles within the fluid having a hydrodynamic size larger than a critical size migrate along the line-of-sight in the array, whereas those having a hydrodynamic size smaller than the critical size follow the flow in a different direction. Flow in the device generally occurs under laminar flow conditions. In the device, particles of different shapes may behave as if they have different sizes. For example, lymphocytes are spheres of ~5 µm diameter, and erythrocytes are biconcave disks of ~7 µm diameter, and ~1.5 µm thick. The long axis of erythrocytes (diameter) is larger than that of the lymphocytes, but the short axis (thickness) is smaller. If erythrocytes align their long axes to a flow when driven through an array of posts by the flow, their hydrodynamic size is effectively their thickness (~1.5 µm), which is smaller than lymphocytes. When an erythrocyte is driven through an array of posts by a hydrodynamic flow, it tends to align its long axis to the flow and behave like a ~1.5 µm-wide particle, which is effectively "smaller" than lymphocytes. The area for deterministic lateral displacement may therefore separate cells according to their shapes, although the volumes of the cells could be the same. In addition, particles having different deformability behave as if they have different sizes. For example, two particles having the undeformed shape may be separated by deterministic lateral displacement, as the particle with the greater deformability may deform when it comes into contact with an obstacle in the array and change shape. Thus, separation in the device may be achieved based on any parameter that affects hydrodynamic size including the physical dimensions, the shape, and the deformability of the particle.

Additional information about microfluidic channel networks and their fabrication can be found, for example, in U.S. Patent App. Publication No. 2011/0091987, U.S. Pat. Nos. 8,021,614, and 8,186,913, each of which is disclosed herein by reference in its entirety.

Figure 8:
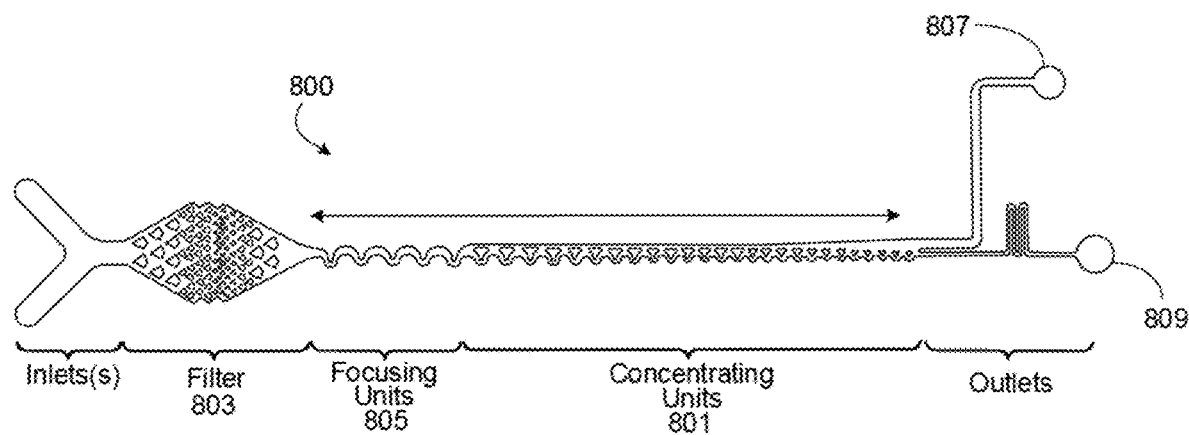
FIG. 8 is a schematic that illustrates an example of a microfluidic system that includes a particle shifting area.

In some implementations, a microfluidic system includes components for preparing a particle carrying fluid sample prior to introducing the fluid into a particle shifting area. For instance, FIG. 8 is a schematic that illustrates an example of a microfluidic system 800 that includes a particle focusing area 801 (labeled "Concentrating units"), similar to the particle focusing area shown in FIG. 5 that relies on inertial focusing and siphoning/fluid extraction for increasing particle to fluid concentration and/or for obtaining a low particle concentration fluid. The system 800 additionally includes a filter section 803 (labeled "Filter") and a particle focusing section 805 (labeled "Focusing Units") upstream from the particle shifting area 801. The filter section 803 includes an arrangement of multiple different-sized post structures.

Based on the arrangement of the structures, the filter section 803 is configured to filter particles contained in an incoming fluid according to the particle size (e.g., average diameter), such that only particles of a pre-defined size or less are able to pass to the next stage of the system 800. For instance, for complex matrices, such as bone marrow aspirate, the filter section 803 may be configured to remove bone chips and fibrin clots to improve the efficiency of enhancing concentration downstream. In an example arrangement, the filter section 803 may include an array of posts having a pillar size and array offset designed to deflect particles above a certain size, thereby separating them from the main suspension. Typically, the size limit is determined based on the maximum particle size that can pass through later stages of the system 800. For example, the filter 803 may be configured to filter/block passage of particles that have an average diameter greater than 50%, greater than 60%, greater than 70%, greater than 80% or greater than 90% of the minimum width of a channel in the particle shifting area 801.

The filter section 803 is fluidly coupled to the particle focusing section 805. The particle focusing section 805 is configured to pre-focus particles exiting the filter section 803 to a desired fluid streamline position, before the particles are provided to the particle shifting area 801. An advantage of pre-focusing the particles is that it reduces the distribution of particles across the channel width to a narrow lateral extent. The focused line of particles then can be repositioned so that the probability of the particles inadvertently entering the wrong channel (e.g., the channel for obtaining "filtered" fluid in the particle shifting area 801) is reduced. Pre-focusing can be achieved using inertial focusing techniques. Further details of inertial focusing are described above in the section entitled "Particle Shifting Using Inertial Focusing."

Once the particle to fluid concentration has been increased in the particle shifting area 801, the "filtered" fluid and/or the particles may be coupled to a separate processing region of the microfluidic system 800 or removed from the system 800 for additional processing and/or analysis. For example, the second channel of the particle shifting area 801 is coupled to a first outlet 807, whereas the first channel of the particle shifting area 801 is coupled to a second outlet 809.

External Forces

Other functionality may be added to the microfluidic system to enhance the focusing, concentrating, separating, and/or mixing of particles. For instance, in some implementations, additional forces may be introduced which result in target specific modification of particle flow. The additional force may include, for example, magnetic forces, acoustic forces, gravitational/centrifugal forces, electrical forces, and/or inertial forces.

FIGS. 9A-9C are schematics illustrating three different examples of microfluidic devices that rely on magnetophoresis used together with the particle shifting techniques described herein to focus different types of particles along different corresponding streamlines within a microfluidic device. In general, magnetophoresis employs high magnetic field gradients for sorting magnetically labeled particles flowing within a microfluidic channel of a device. The magnetic field gradients are produced by placing one or more magnets adjacent to the microfluidic channel, in which the configuration of the magnets gives rise to a magnetic flux gradient profile that extends across the microfluidic channel. The magnetically labeled particles are subsequently "pulled" by the gradient. Depending on the positioning of the gradient profile, the magnetically labeled particles can be focused to one or more desired positions within the microfluidic channels. Further details on the application of magnetophoresis to microfluidic devices can be found, for example, in WO 2014/004577, incorporated herein by reference in its entirety.

In the first example shown in FIG. 9A, a microfluidic device 900a includes a particle shifting area 901 fluidly coupled to magnetophoresis area 703. The particle shifting area (labeled "Focusing" in FIG. 9A) 901 is constructed in a similar manner as the device 100 shown in FIG. 1. Briefly, the focusing area 901 includes two separate fluid flow regions: a second fluid flow region and a first fluid flow region separated by a ID array of island structures, each of which is separated from an adjacent island structure by a gap. As fluid propagates through the first flow region, a portion of the fluid is extracted into the second flow region, while an inertial lift force is exerted on the particles, which keeps the particles traveling within the first flow region. Of course, other forces (such as inertial focusing) may be used in addition or as an alternative to keep particles within the first fluid flow region. Both the second and first fluid flow regions of the particle shifting area are fluidly coupled into the magnetophoresis area 903, which is void of island structures.

The magnetophoresis area 903 is configured to include a magnetic field gradient that extends across the microfluidic channel. For example, the microfluidic device 900a may include one or more magnets 907 adjacent to the magnetophoresis area 903, in which the magnets 907 create the magnetic field gradient. For ease of illustration, the magnets 907 are shown at the bottom of the page to indicate their position relative to the microfluidic devices (900a, 900b, and 900c) along the longitudinal direction of fluid flow. However, it should be understood that in operation, the magnets 907 are more likely to be positioned above and/or below the fluidic channel in the magnetophoresis area 903 (i.e., along the x-axis in FIGS. 9A-9C) of each of the devices 900a, 900b and 900c.

Referring again to FIG. 9A, two different types of particles are included in the fluid introduced into the focusing area 901. A first type of particle may include a desired analyte (e.g., a cell, platelet, or bacteria) that is bound to a magnetic marker such as a magnetic bead. The second type of particle may include a second analyte that has no substantial magnetic component. As the two different types of particles pass through the focusing area 901, the particles are concentrated in the first fluid flow region and are focused along a fluid streamline. The focused particles then pass into the magnetophoresis area 903, where the magnetic field gradient exerts a force on the particles bound to the magnetic beads. The force generated by the interaction of the field gradient with the magnetic beads causes the magnetically labeled particles to deviate from the propagation direction of the original fluid streamline. In particular, the magnetically labeled particles follow the magnetic gradient and form a new stream of particles. The direction of the magnetic gradient, and thus the path that the magnetically labeled particles follow may depend on the orientation and arrangement of the magnets 907 near the magnetophoresis area 903. The two different streams of particles, i.e., a stream containing magnetically labeled particles and a stream of non-magnetically labeled particles, then may be separately collected at an output of the magnetophoresis area 903 (referred to as "labeled particles" and "unlabeled particles" in FIG. 9A).

In the second example shown in FIG. 9B, the particle shifting area is constructed in a similar manner as the device 200 in FIG. 2. Again, a fluid containing a first type of particle that is bound to a magnetic marker and a second type of particle that has no substantial magnetic component is introduced into the focusing area 901. The fluid shifting and inertial lift forces (or, e.g., inertial focusing forces) focus both types of particles within a first fluid flow region between two arrays of island structures. The focused particles then exit the particle shifting area and are fluidly coupled into the microfluidic channel of the magnetophoresis area 903. Once the particles enter the magnetophoresis area 903, the magnetic field gradient generated by the magnets 907 exerts a force on the magnetically labeled particles, causing them to diverge from the propagation direction of the original focused stream. In the example of FIG. 9B, the stream of particles flowing from the focusing area 901 include a first set of magnetically labeled particles, a second set of magnetically labeled particles, and a third set of non-labeled particles. As shown in FIG. 9B, the gradient is arranged such that the magnetically labeled particles are deflected either to the top or bottom of the channel, whereas the non-labeled particles continue to follow their original focused trajectory through the magnetophoresis area 703. Again, the labeled and unlabeled particles, once separated, may be collected at an output of the magnetophoresis area 903 for extraction or further analysis.

The third example shown in FIG. 9C demonstrates sorting of particles in a manner opposite to that of FIG. 9B. The focusing area 901 in FIG. 9C is constructed in a similar manner to the device 300 shown in FIG. 3. In particular, the focusing area 901 includes an initial island structure configured to separate an incoming fluid containing magnetically labeled and non-labeled particles into two separate channels (i.e., a second fluid channel (upper channel in FIG. 9C) and a third fluid channel (lower channel in FIG. 9C), where the particles are focused into streamlines. Once the focused streams of particles pass into the microfluidic channel of the magnetophoresis area 903, the magnetic field gradient generated by the magnets 907 causes the magnetically labeled particles to diverge towards the center of the first channel (center channel in FIG. 9C) and form a third focused stream. After deflection by the magnetic gradient, the second and third streams are left with unlabeled particles. Again, both the unlabeled and labeled particles, once separated, may be collected at an output of the magnetophoresis area 903 for extraction or further analysis.

While the examples shown in FIGS. 9A-9C perform the focusing and magnetic separation of particles in separate stages, such functions can be performed in a single stage. FIGS. 9D-9F are schematics illustrating three different examples of microfluidic devices (900d, 900e, 900f) that rely on the use of magnetophoresis with the particle shifting techniques described herein to focus different types of particles along different corresponding streamlines in a single stage. Again, the microfluidic devices 900 include one or more magnets 907 to create the magnetic field gradient. The magnets 907 in FIGS. 9D-9F are shown at the bottom of the page to indicate their position relative to the microfluidic devices (900d, 900e, and 900f) along the longitudinal direction of fluid flow. However, it should be understood that in operation, the magnets 907 are more likely to be positioned above and/or below the fluidic channel in the magnetophoresis area 903 (i.e., along the x-axis in FIGS. 9D-9F) of each of the devices 900d, 900e, and 900f.

Referring to FIG. 9D, the focusing area is constructed in a similar manner as the device 100 shown in FIG. 1. That is, the focusing area includes a second microfluidic channel separated from a first microfluidic channel by an array of island structures. In contrast to FIGS. 9A-9C, the magnetic field gradient from the magnets 907 extends across both the second and first fluid flow regions of the focusing area. When a fluid containing both magnetically labeled particles and unlabeled particles is introduced into the particle shifting area, the particles are initially constrained within the first microfluidic channel due to inertial lift forces. However, the magnetically labeled particles may experience a force (depending on the arrangement of the magnetic field gradient) from the magnetic field that overcomes the inertial lift force. In certain implementations, the magnetically generated force may cause the labeled particles to diverge from the stream of unlabeled particles and pass through openings between the island structures.

FIGS. 9E-9F are schematics illustrating alternative configurations of microfluidic devices that combine particle shifting areas with magnetophoresis. Similar to the example of FIG. 9D, the examples shown in FIGS. 9E-9F illustrate how a magnetic field gradient can cause magnetically labeled particles to diverge from an initially focused stream of particles and form new focused particles streams. In FIG. 9E, magnetically labeled particles are deflected through openings between island structures to a second (upper channel in FIG. 9E) and third (lower channel in FIG. 9E) microfluidic channel, whereas a focused stream of non-labeled particles remain within a first (center channel in FIG. 9E) microfluidic channel that is located between the two arrays of island structures. In FIG. 9F, the inertial lift forces near the island structures maintain the non-labeled particles along focused streams within a second (upper channel in FIG. 9F) and third (lower channel in FIG. 9F) microfluidic channel. In contrast, a magnetic field gradient generated by the magnets 907 causes magnetically labeled particles to pass through openings in the island structures into a center microfluidic channel that is located between the second and third microfluidic channels.

The magnetic markers used for labeling particles can include spherical bead-like materials having one or more inner magnetic cores and an outer coating, e.g., a capping polymer. The magnetic cores can be monometallic (e.g., Fe, Ni, Co), bimetallic (e.g., FePt, SmCo, FePd, and FeAu) or can be made of ferrites (e.g., $Fe_2O_3$, $Fe_3O_4$, $MnFe_2O_4$, $NiFe_2O_4$, $CoFe_2O_4$). The magnetic markers can be nanometers or micrometers in size, and can be diamagnetic, ferromagnetic, paramagnetic, or superparamagnetic, in which size corresponds to an average diameter or average length. For example, the magnetic markers can have a size of approximately 1 µm, approximately 600 nm, approximately 500 nm, approximately 300 nm, approximately 280 nm, approximately 160 nm, or approximately 100 nm. Other marker sizes are possible as well. The outer coating of a marker can increase its water-solubility and stability and also can provide sites for further surface treatment with binding moieties. The magnetic markers each have a magnetic moment in the range of about 1 KA/m to about 100 kA/m. For example, in some implementations, the magnetic markers have a magnetic moment of about 35 kA/m In general, the magnetic markers may be bound to target analytes in a fluid using binding moieties. A binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target.

In certain embodiments, the binding moieties can be designed or selected to serve, when bound to another binding moiety, as substrates for a target molecule such as enzyme in solution. Binding moieties include, for example, oligonucleotides, polypeptides, antibodies, and polysaccharides. As an example, streptavidin has four sites (binding moieties) per molecule that will be recognized by biotin. For any given analyte, e.g., a specific type of cell having a specific surface marker, there are typically many binding moieties that are known to those of skill in the relevant fields.

For example, certain labeling methods and binding moiety techniques are discussed in detail in U.S. Pat. No. 6,540,896 entitled, "Microfabricated Cell Sorter for Chemical and Biological Materials" filed on May 21, 1999; U.S. Pat. No. 5,968,820 entitled, "Method for Magnetically Separating Cells into Fractionated Flow Streams" filed on Feb. 26, 1997; and U.S. Pat. No. 6,767,706 entitled, "Integrated Active Flux Microfluidic Devices and Methods" filed on Jun. 5, 2001.

The surface of the magnetic markers can be treated to present functional groups (e.g., —$NH_2$, —COOH, —HS, —$C_nH_{2n-2}$) that can be used as linkers to subsequently attach the magnetic markers to the target analytes (e.g., antibodies, drugs). In some cases, the surface treatment makes the magnetic markers essentially hydrophilic or hydrophobic. The surface treatment can include the use of polymers including, but not limited to, synthetic polymers such as polyethylene glycol or silane, natural polymers, derivatives of either synthetic or natural polymers, and combinations thereof.

In some implementations, the surface treatment does not result in a continuous film around the magnetic marker, but results in a "mesh" or "cloud" of extended polymer chains attached to and surrounding the magnetic marker. Exemplary polymers include, but are not limited to, polysaccharides and derivatives, such as dextran, pullanan, carboxydextran, carboxmethyl dextran, and/or reduced carboxymethyl dextran, PMMA polymers and polyvinyl alcohol polymers. In some implementations, these polymer coatings provide a surface to which targeting moieties and/or binding groups can bind much easier than to the marker. For example, in some embodiments magnetic markers (e.g., iron oxide nanoparticles) are covered with a layer of 10 kDa dextran and then cross-linked with epichlorohydrin to stabilize the coating and form cross-linked magnetic markers.

Additional information on the fabrication, modification, and use of magnetic markers can be found, for example, in PCT Pub. No. WO/2000/061191, U.S. Patent App. Pub. No. 20030124194, U.S. Patent App. Pub. No. 20030092029, and U.S. Patent App. Pub. No. 20060269965, each of which is incorporated herein by reference in its entirety.

Fabrication of Microfluidic Devices

A process for fabricating a microfluidic device according to the present disclosure is set forth as follows. A substrate layer is first provided. The substrate layer can include, e.g., glass, plastic or silicon wafer. An optional thin film layer (e.g., $SiO_2$) can be formed on a surface of the substrate layer using, for example, thermal or electron beam deposition. The substrate and optional thin film layer provide a base on which microfluidic regions may be formed. The thickness of the substrate can fall within the range of approximately 500 µm to approximately 10 mm. For example, the thickness of the substrate 210 can be 600 µm, 750 µm, 900 µm, 1 mm, 2 mm, 3 mm, 4 mm, 5 mm, 6 mm, 7 mm, 8 mm, or 9 mm. Other thicknesses are possible as well.

After providing the substrate layer, the microfluidic channels formed above the substrate layer. The microfluidic channels include the different fluid flow pathways of the particle shifting area, as well as the other microfluidic components of the system, including any filtering sections, inertial focusing sections, and magnetophoresis sections. Microfluidic channels for other processing and analysis components of a microfluidic device also may be used. The microfluidic channels and cover are formed by depositing a polymer (e.g., polydimethylsiloxane (PDMS), polymethylmethacrylate (PMMA), polycarbonate (PC), or cyclo olefin polymer (COP)) in a mold that defines the fluidic channel regions. The polymer, once cured, then is transferred and bonded to a surface of the substrate layer. For example, PDMS can be first poured into a mold (e.g., an SU-8 mold fabricated with two step photolithography (MicroChem)) that defines the microfluidic network of channels. The PDMS then is cured (e.g., heating at 65° C. for about 3 hours). Prior to transferring the solid PDMS structure to the device, the surface of the substrate layer is treated with $O_2$ plasma to enhance bonding. Alternatively, the microfluidic channels and cover can be fabricated in other materials such as glass or silicon.

APPLICATIONS

The new microfluidic techniques and devices described herein can be used in various different applications.

Centrifugation Replacement

The particle shifting techniques and devices disclosed herein can be used as replacements for centrifugation. In general, centrifugation is understood to include the concentrating of sub-components within a fluid through the application of centrifugal forces to the fluid. Typically, this process requires devices that have moving parts, which are prone to wear and breakage. Moreover, the moving parts require complex and costly fabrication processes. Another problem with centrifugation is that it is a process typically applied in a closed system, i.e., centrifugation requires manually transferring samples to and from a centrifuge.

In contrast, the presently disclosed techniques are capable of substantially increasing the concentration of fluid components using relatively simple micro-structures without the need for moving parts. The techniques can be implemented as part of a single open microfluidic system, such that fluid samples may be transferred to or from the particle shifting area without manual interference. Additionally, particle shifting can be extended to devices requiring large throughput (i.e., volume rate of fluid that can be processed). For example, the devices disclosed herein may be configured to enable up to 10, 25, 50, 75, 100, 250, 500, 1000, 5000, or 10000 μl/min of fluid flow. Other flow rates are also possible. For instance, using device 100 in FIG. 1 as an example, if the second and first microfluidic channels 106, 108 have depths of approximately 50 μm and widths of approximately 50 μm, the device 100 may be capable of achieving a combined sample flow rate of up to about 5 mL/min. Varying the channel sizes may alter the maximum volumetric flow rate of which the device is capable. Furthermore, multiplexing multiple channels may enable even higher rates of flow. Thus, in certain implementations, the particle shifting techniques may provide substantial cost and time saving advantages over traditional centrifugation processes. Examples of applications where a microfluidic replacement for a centrifuge device may be useful include bone marrow and urine analysis.

Detecting Infectious Agents

In addition, the particle shifting techniques disclosed herein can be used as part of a research platform to study analytes of interest (e.g., proteins, cells, bacteria, pathogens, and DNA) or as part of a diagnostic assay for diagnosing potential disease states or infectious agents in a patient. By separating and focusing particles within a fluid sample, the microfluidic device described herein may be used to measure many different biological targets, including small molecules, proteins, nucleic acids, pathogens, and cancer cells. Further examples are described below.

Rare Cell Detection

The microfluidic device and methods described herein may be used to detect rare cells, such as circulating tumor cells (CTC) in a blood sample or fetal cells in blood samples of pregnant females. For example, the concentration of primary tumor cells or CTCs can be enhanced in a blood sample for rapid and comprehensive profiling of cancers. By combining the particle deflection techniques described herein with magnetophoresis (see FIG. 7), different types of cells can be detected (e.g., circulating endothelial cells for heart disease). Thus, the microfluidic device may be used as a powerful diagnostic and prognostic tool. The targeted and detected cells could be cancer cells, stem cells, immune cells, white blood cells or other cells including, for example, circulating endothelial cells (using an antibody to an epithelial cell surface marker, e.g., the Epithelial Cell Adhesion Molecule (EpCAM)), or circulating tumor cells (using an antibody to a cancer cell surface marker, e.g., the Melanoma Cell Adhesion molecule (CD146)). The systems and methods also can be used to detect small molecules, proteins, nucleic acids, or pathogens.

Fluid Exchange

The microfluidic device and methods described herein may be used to shift cells from one carrier fluid to another carrier fluid. For example, the particle shifting techniques disclosed could be used to shift cells into or out of a fluid stream containing reagents, such as drugs, antibodies, cellular stains, magnetic beads, cryoprotectants, lysing reagents, and/or other other analytes.

A single particle shifting region could contain many parallel fluid streams (from many inlets) through which a shifted cell would pass. For example, white blood cells could be shifted from a blood stream into a stream containing staining reagents and then into a buffer stream.

In bioprocessing and related fields, the devices and techniques described may be used to enable sterile, continuous transfer of cells from old media (containing waste products) into fresh growth media. Similarly, extracellular fluids and cellular products (e.g., antibodies, proteins, sugars, lipids, biopharmaceuticals, alcohols, and various chemicals) may be extracted from a bioreactor in a sterile, continuous manner while cells are retained within the bioreactor.

Fluid Sterilization and Cleansing

The microfluidic device microfluidic device and methods described herein may be used to remove pathogens, pollutants, and other particular contaminants from fluids. By shifting contaminants across fluid streamlines, contaminants may be removed from a fluid sample and collected as a separate waste stream.

Harvesting Algae for Biofuels

Harvesting algae from growth media is a major expense in the production of biofuels because algae grow in very dilute suspensions at near neutral buoyancy, making efficient extraction and concentration of algal biomass difficult. The microfluidic device and methods described herein can provide an efficient means of harvesting algae that does not depend on either density or filtration. The devices and techniques described enable the algae in a growth tank to be extracted from the growth media and concentrated to a high volume density. This can be done either as a single step or as part of a continuous process. Additionally, because the devices described herein can sort cells in a size-dependent manner, they can be designed to sort and concentrate only the larger algae that have reached maturity, returning smaller, immature algae to the growth tank.

EXAMPLES

The invention is further described in the following examples, which do not limit the scope of the invention described in the claims.
Device Fabrication Various experiments were performed to analyze the behavior of microfluidic devices having asymmetrically curved channels (see, e.g., the section above entitled "Increasing Particle Concentration/Reducing Fluid Volume" and the device shown in FIG. 5) that combine inertial focusing with fluid extraction to achieve volume reduction of particle-rich fluid samples. That is, the devices included a focusing channel (see, e.g., channel 508 in FIG. 5) in which particles were focused using inertial focusing techniques and a particle-free channel/second fluid flow channel (see, e.g., channel 506 in FIG. 5) into which fluid from the focusing channel was extracted. The experiments are described in Examples 1 to 5 below. The devices used in those examples were designed and fabricated as follows.

For each microfluidic device, standard SU8 photolithography and soft lithography techniques were used to fabricate the master mold and the PDMS microchannels, respectively. Briefly, negative photoresist SU8-50 (Microchem Corp, Massachusetts) was spun at 2850 RPM to a thickness of approximately 50 µm, exposed to ultraviolet light through a mylar emulsion printed photomask (Fineline Imaging, Colorado) that defines the microfluidic network of channels, and developed in BTS-220 SU8-Developer (J. T. Baker, New Jersey) to form a raised mold. A 10:1 ratio mixture of Sylgard 184 Elastomer base and curing agent (Dow Corning, Michigan) was then poured over the raised mold, allowed to cure in an oven at 65° C. for 8 hours and then removed from the SU8 master mold to form the microfluidic device cover having the patterned channels. Inlet and outlet holes to the channels were punched using custom sharpened needle tips. The devices were then cleaned of particulate using low-residue tape and oxygen plasma bonded to pre-cleaned 1 mm thick glass microscope slides.

For experiments where high pressure deformation of PDMS was a concern, epoxy devices were used instead. Epoxy devices were constructed using PDMS molds created by treating PDMS channels with tridecafluoro-1,1-2,2-tetrahydrooctyl-trichlorosilane (Gelest) and then pouring PDMS over the silanized channels. After 24 hours of curing at 65° C., the molds were carefully separated from the silanized channels. Holes were punched into PDMS molds at the inlets and outlets using a 0.75 mm diameter Harris Uni-Core biopsy punch. Teflon coated wire (0.028 inch diameter, McMaster-Carr) was inserted gently into these holes as to not deform the surface of the PDMS mold. Tygon tubing (0.02" I.D., 0.06" O.D.) was then guided onto teflon coated wire and suspended ~1 mm from the mold surface. Epoxacast 690 (Smooth-On) was mixed and degassed for 30 minutes prior to pouring into the mold. At the same time as molds were filled, slides were coated with epoxy by laying a glass slide on a drop of epoxy atop a flat PDMS surface.

After ~28 hours, the devices were cooled temporarily to −22° C. to prevent deformation, the Teflon wire was removed and devices removed from the molds. Then the glass slides were removed from the PDMS slabs and heated to 55° C. and devices were pressed against slides ensuring bonding.
Particle and Cell Suspensions The devices used in the Examples described below were tested over a wide range of flow conditions using fluorescent polystyrene beads and white blood cells as exemplar particles. Polystyrene particle suspensions were created using 4.4 µm diameter blue-fluorescent beads (Polysciences), 9.9 µm diameter green-fluorescent beads (ThermoFisher Scientific) and 15 µm diameter red-fluorescent beads (Invitrogen). Each was suspended to a final length fraction of 0.1 in an equivalent density solution (1.05 g/mL) of 1×PBS, 0.1% Tween20, and iodixanol. White blood cells (buffy coat) were isolated using deterministic lateral displacement with a co-flow of buffer solution.
Fluorescent Counting and Cell Counting Fluorescent and high resolution imaging of fluid samples were accomplished using an automated Nikon TiE inverted microscope with a Retiga 2000R monochromatic camera as well as a Vision Research Phantom v4.2 high speed monochromatic camera.

Hemocytometers and Nageotte chambers were utilized for measuring particle concentrations in white blood cell yield experiments at dilutions dependent upon the output cell concentrations.

Example 1: Cell Free Layer Growth and Siphon Percentage

The combined siphoning and inertial focusing design takes advantages of fast-acting inertial forces, which generate a particle-free layer near the walls of the microfluidic channel. This particle-free fluid layer then is controllably siphoned off leaving the particles once again closer to the walls where the inertial forces are strongest. The process of focusing and siphoning may be repeated until a desired volume reduction is achieved. When using a microfluidic device to enhance the concentration of particles within a fluid or to extract a particle-free fluid, an important design consideration may include controlling the percentage of fluid that is siphoned relative to the dynamics of the formation of the particle-free layer. In inertial focusing systems, the focusing behavior is a cumulative result of numerous parameters including the channel geometry as well as flow speed (See, e.g., Di Carlo, D. "Inertial microfluidics," Lab Chip 9, 3038 (2009) and Martel, J. & Toner, M. "Inertial Focusing in Microfluidics," Annual Review of Biomedical Engineering 16, 371-396 (2014), incorporated herein by reference in their entirety). For instance, curved structures are generally more efficient than planar structures at achieving focusing over a given channel length while in some implementations are also more sensitive to changes in flow speed.

Using asymmetrically curved structures similar to the structures described with respect to FIGS. 5-6, we characterized the formation of a particle-free layers for a range of focusing channel widths (between 50 µm to 200 µm) and over a range of flow rates (between 10 µL/min and 3000 µL/min) depending on the channel width. Each of the devices tested included a series of five focusing-siphoning unit pairs (see, e.g., FIG. 6) followed by an expansion into a 500 µm wide straight section. The particle-free layer width of the resulting output fluid was measured downstream of the focusing units after the channel had fully expanded based on a 10% relative intensity threshold across the channel width (i.e., the intensity is normalized to between 0% to 100%, after which the position at which the intensity reaches 10% is identified. See, e.g., Martel, J. M. & Toner, M. "Particle Focusing in Curved Microfluidic Channels," Sci. Rep. 3, 1-8 (2013), incorporated herein by reference in its entirety).

Figure 10:
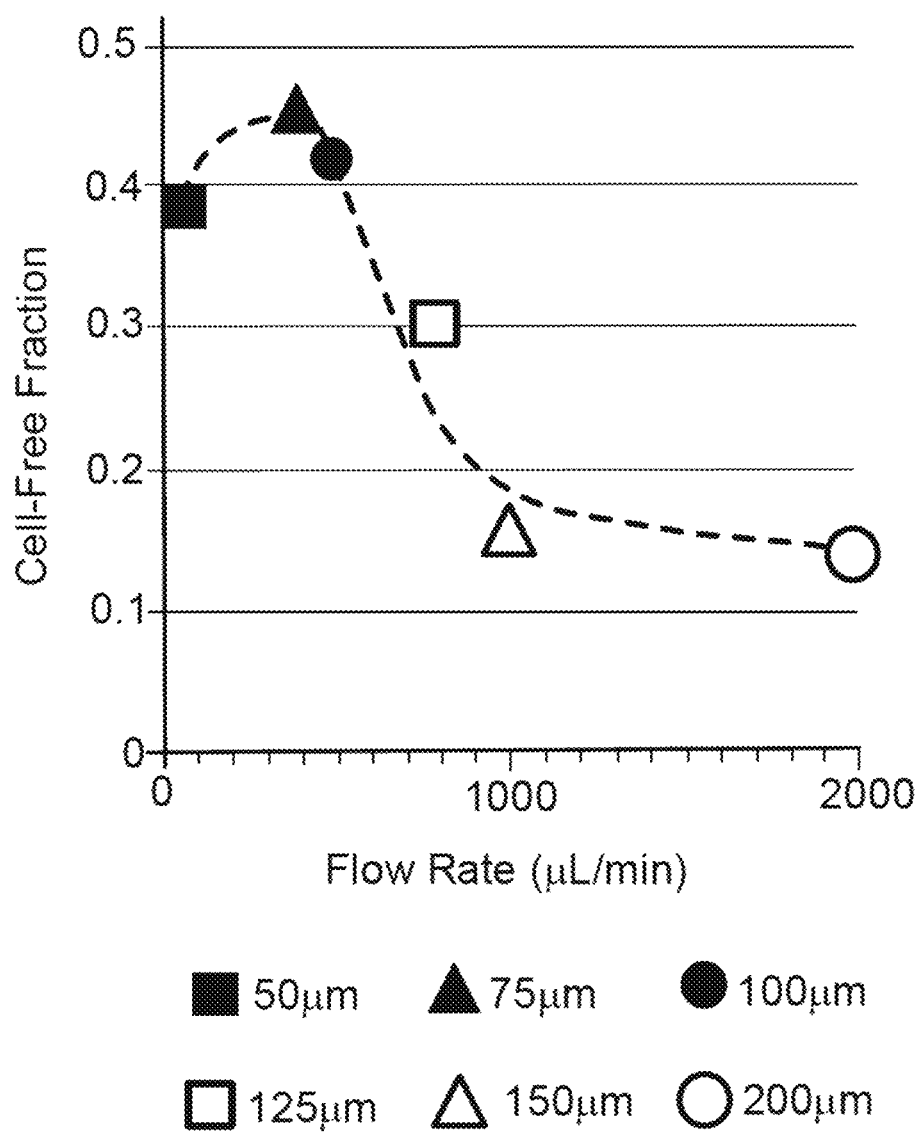
FIG. 10 is a plot of cell-free fraction versus sample flow rate through a microfluidic device.
Figure 11A:
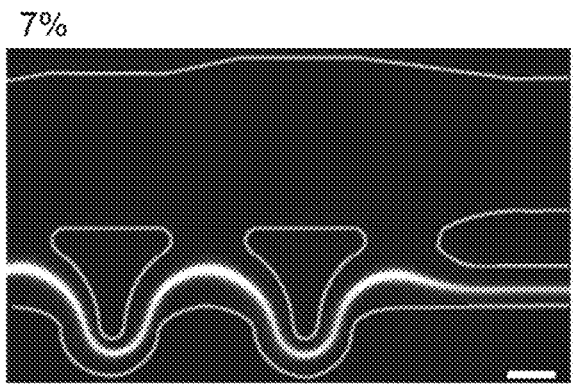
FIGS. 11A-11D are photographs of fluorescently tagged particles flowing through focusing-siphoning units of a microfluidic device for different siphon percentages.
Figure 11C:
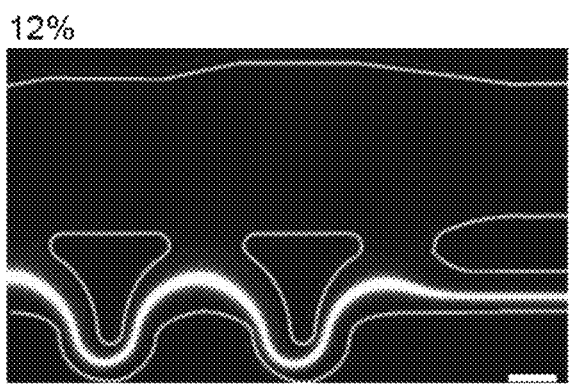
Figure 11B:
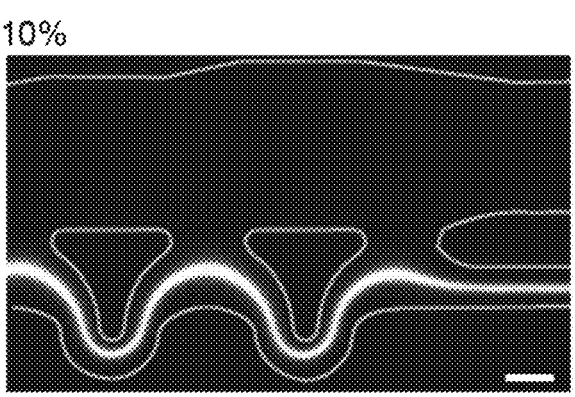
Figure 11D:
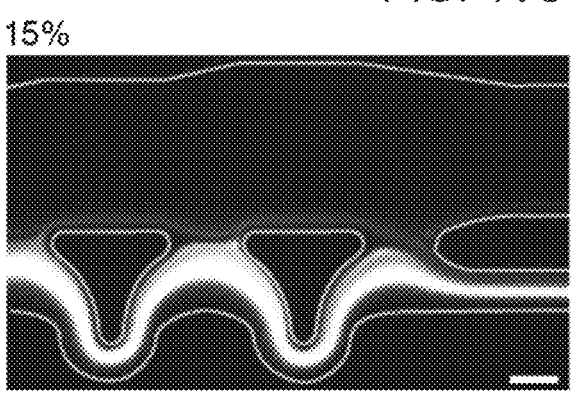

The width of the particle-free layer at the optimal flow rate for each channel width was compared to one another as shown in FIG. 10. Specifically, FIG. 10 shows the "cell-free fraction" versus flow rate, in which each of the data points represents the maximum fraction of the fluid (as measured across the channel width) that is free of particles for each different sized channel. The legend beneath the plot indicates the channel widths. As is evident from the graph shown in FIG. 10, the narrower channels achieve significantly higher maximum particle-free layer width than the wider channels (50 µm wide-38%, 75 µm-46%, 100 µm-42%, 125 µm-30%, 150 µm-15%, 200 µm-13%). The variation in particle-free layer width over a range+/−50% of the optimal flow rate (flow rate which achieves the maximum particle-free layer width) was lower for the wider channels (50 µm wide-12%, 75 µm-23%, 100 µm-16%, 125 µm-15%, 150 µm-4.6%, 200 µm-5.5%).

Using the reference data we determined that there was a nearly linear relationship between the optimal flow rate, $Q_{Optimal}$ (i.e., the flow rate that resulted in the greatest width for particle-free layer formation), and the focusing unit width, $w_{focus}=1.0911e^{-07}*Q_{Optimal}(\mu L/min)+4.4789E^{-05}$ m. Based on the foregoing relationship, it is possible to create a device that maintains a high level of particle-free layer formation efficiency as fluid is siphoned from the focusing channel and as the flow rate through the focusing channels decreases.

The relationship between the formation of the particle-free layer and a maximum siphon percentage was also studied. The siphon percentage is the percentage of flow in the focusing channel that is siphoned out at the next opening between islands. The amount siphoned is determined by the relative fluidic resistances of the focusing and siphon channels. In particular, a set of devices was designed using a range of siphon percentages (7%, 10%, 12% and 15%) for a fixed input flow rate of 500 µL/min. The flow rate of 500 µL/min was chosen to be within the optimal flow rate range of the narrower more efficient focusing unit widths. A comparison of the focusing performance of these devices indicates that, depending on the volume reduction factor desired, the siphon percentage must be below 10% for a factor of 10 volume reduction and 7% for a factor of 50 volume reduction. The volume reduction factor is equivalent to the concentration factor and may be expressed as one divided by the fraction of flow in the focusing channel. For example, if 5% of the total flow is in the focusing channel, the volume reduction factor is 20. FIG. 11 includes images of fluorescently tagged white blood cells flowing through the focusing-siphoning units of the microfluidic device, in which each image corresponds to a different siphon percentage for a factor of 10 volume reduction. As is evident from the images, the loss of particles from the focusing channel into the second fluid flow channel in the 15% siphon percentage device is quite noticeable.

As the foregoing results demonstrate, the combined siphoning and inertial focusing techniques enable the control of the volume reduction factor in a well-regulated manner. In some implementations, it may be possible to obtain a specific volume reduction factor thereby tailoring a specific sample volume for downstream molecular assays independent of the input sample volume.

For the experiments described below, we have selected two specific designs for detailed characterization. The two selected designs are a factor of 10 ("10×") concentrator (this device included 26 focusing-siphoning unit pairs and had a 10% siphon percentage) and a factor of 50 ("50×") concentrator (this device included 152 focusing-siphoning unit pairs and had a 7% siphon percentage).

Example 2: Flow Rate Dependence

Another factor that may be considered in a microfluidic system for performing volume reduction and/or increasing the particle concentration within a fluid is the flow speed of the fluid sample through the microfluidic device. Accordingly, the sensitivity to flow rate was also investigated. Using isolated white blood cells (buffy coat), the yields of both the 10× and 50× devices were analyzed between input flows rates of 100 µL/min and 1000 µL/min. Yield is calculated on a relative basis between the number of cells in the stream flowing in the focusing channel and the number of cells in the second fluid flow region or, alternatively, as the total number of cells in the stream flowing in the focusing channel divided by total cells in the focusing channel and the second fluid flow channel combined. A high yield of greater than 95% for the devices was maintained between 400 and 600 µL/min but beyond that the drop off in yield began to be significant. For instance, multiple separate streams containing the white blood cells began to form at 1000 µL/min.

Figure 12:
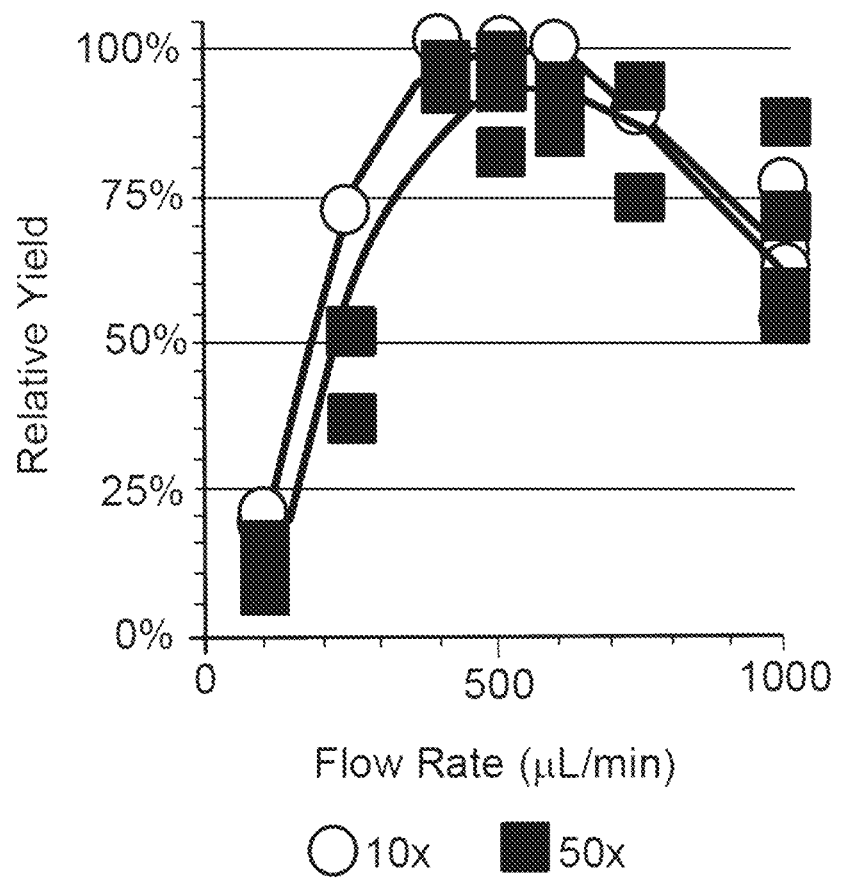
FIG. 12 is a plot of relative white blood cell yield versus flow rate.

FIG. 12 is a plot of relative white blood cell yield versus flow rate for both the 10× and 50× devices. In general, the system loss (e.g., due to cells lost in transfers between various containers, in tubing, etc.) comparing the input number of cells to total cells coming out of the focusing channel and the second flow channel combined was typically low, around 10%. For flow rates lower than 400 µL/min, the drop off in yield was consistent with an overall lack of focusing. For example, in the case of negligible inertial effects, one would expect a yield equivalent to the flow split, such as 10% and 2% for the 10× and 50× devices, respectively. The increase in yield by increasing the flow rate from 100 to 400 µL/min was indicative of the improvement of focusing with Reynolds number as inertial effects increase. The decrease in yield after 600 µL/min was a likely a consequence of PDMS deformation at the higher driving pressures leading to significantly different focusing patterns.

The exact range of input and output flow rates depend on the particle size and channel dimensions used. To efficiently achieve higher throughput for a given design, multiplexing of channels may be needed.

Example 3: Size Dependence

Figure 13:
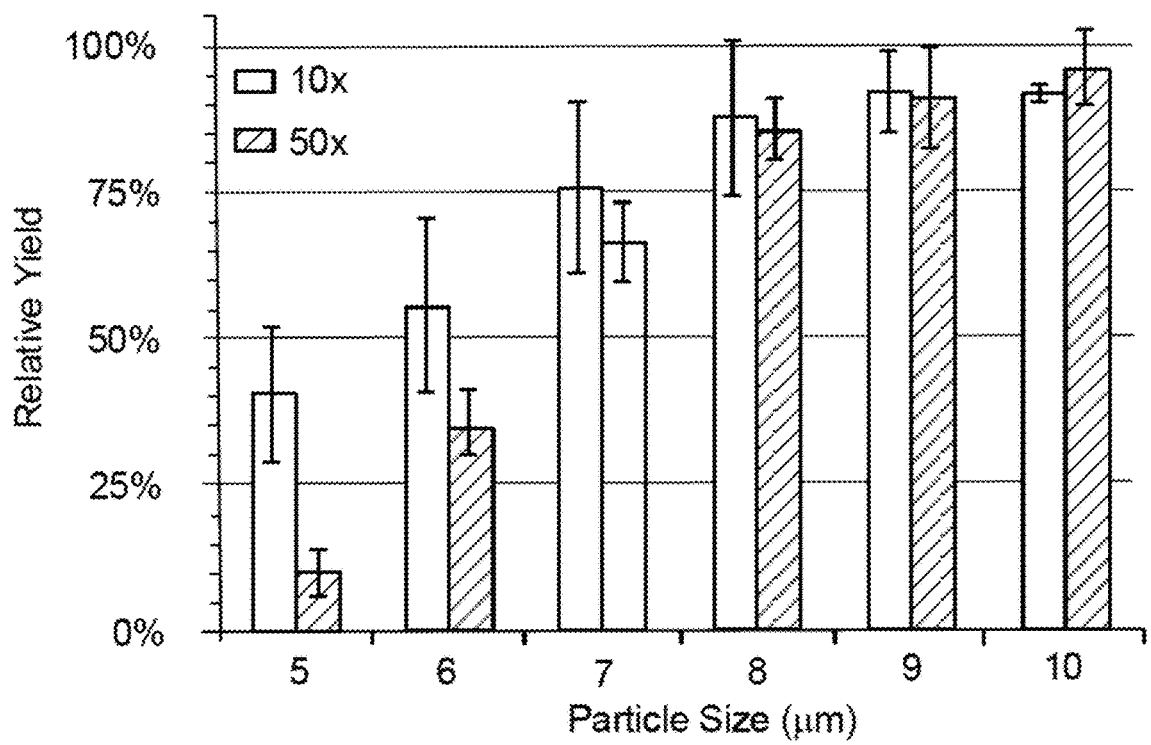
FIG. 13 is a plot of relative particle yield in a microfluidic device versus flow-rate.

Inertial forces are strongly dependent upon the size of the particles being focused. Accordingly, the performance of the combined inertial focusing and siphoning devices were evaluated to understand the sensitivity to particle size. In particular, a variety of polystyrene particle sizes (4 µm-10 µm) were run simultaneously through the 10× and 50× devices in order to determine the size range of particles that are deflected from the focusing channel to the second fluid flow region where the "particle-free" layer was desired. FIG. 13 is a plot of the foregoing experiment and suggests a trend where smaller particle sizes have lower relative yields (i.e., (total cells in product)/(total cells in product+total cells in waste)) compared to larger particle sizes, i.e., the smaller a particle is, the greater the probability that the particle will escape the focusing channel through a gap between island structures. If relative yields above 90% are desired, a cutoff particle size for this threshold can be interpolated as approximately 8.5 μm for the 10× device and approximately 8 μm for the 50× device. This slight difference may be attributed to the significantly lower velocities at the end of the 50× concentrator where the focusing becomes more sensitive to particle size.

The foregoing results showing the sensitivity of the combined siphoning and inertial focusing devices to particle size may lead to several possible advantageous applications. For instance, the size dependence can be beneficial for cleanup of biological samples (e.g., removing bacteria) as particles smaller than a cutoff size will be siphoned off from the focusing channel into the second fluid flow channel, thus improving the final sample purity or decreasing undesired biological sample contamination.

Example 4: Volume Fraction Dependence

Another factor that was analyzed was the effect of inter-particle interactions on the focusing behavior. Generally, conventional inertial focusing devices have a strict requirement that the input fluid sample concentrations be low in order to achieve high quality focusing (see, e.g., Lee, W., Amini, H., Stone, H. A. & Di Carlo, D. "Dynamic self-assembly and control of microfluidic particle crystals," Proceedings of the National Academy of Sciences 107, 22413 (2010), incorporated herein by reference in its entirety). A theoretical concentration limitation is given by the limit of a continuous line of adjacently touching particles at the equilibrium positions along the entire channel length or a length fraction of 1 (see, e.g., Di Carlo, D. "Inertial microfluidics," Lab Chip 9, 3038 (2009), incorporated herein by reference in its entirety). We investigated the operational cutoff of the particle concentration for the 10× and 50× devices by varying the input concentration of white blood cells processed at 500 μL/min.

Figure 14:
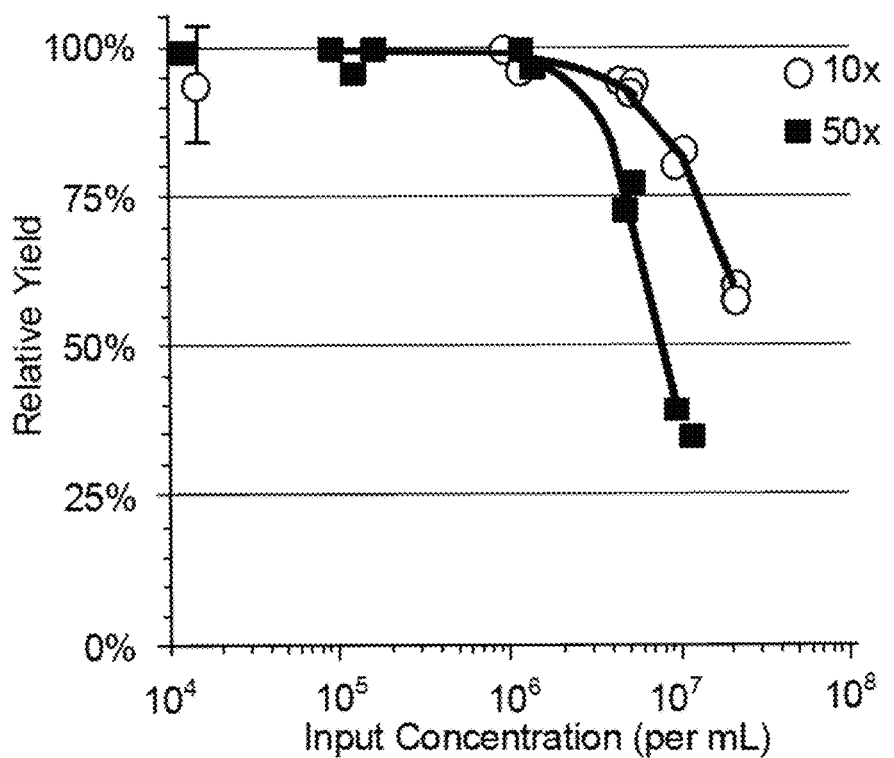
FIG. 14 is a plot illustrating the relative yield of white blood cells within a microfluidic device for different input concentrations.

FIG. 14 is a plot illustrating the relative yield of the white blood cells at this flow rate for different input concentrations. As the plot indicates, there is a sharp maximum limit at an input concentration of approximately 1 million cells per milliliter. The particle concentration at which the particle interactions will start affecting the performance of the device threshold was reached in the devices of approximately at approximately 80M cells per milliliter. This high particle concentration may be attributable to the fact that the operational success or yield of the devices does not require that all of the particles fall on a single streamline. Instead, the cell free layer formation near the walls leads to a much higher concentration at which the yield decreases (i.e., rather than requiring all particles to pack into the limited space of a single narrow stream, we only required that particles be packed into the region of fluid that is not siphoned, which can accommodate far more particles). The foregoing experimental results indicate that the particle-free layer formation is not as sensitive to particle volume fraction as the single stream or high quality inertial focusing as previously understood (see, e.g., Di Carlo, D. "Inertial microfluidics," Lab Chip 9, 3038 (2009), incorporated herein by reference in its entirety).

Example 5: Achieving Greater Than 50× Volume Reduction

We also analyzed the ability of the microfluidic volume reduction devices to obtain substantially high throughputs and volume reduction. For example, in some cases, large numbers of the devices shown in FIGS. 1-5 may be operated in parallel to increase the overall system throughput (i.e., the overall volume of fluid processed). For instance, in one possible design, multiple volume reduction devices (e.g., device 100) may each have a separate fluid input to receive a fluid sample, where the output of each device is coupled to a common output channel for collecting either concentrated particles or the filtered fluid sample.

Figure 15:
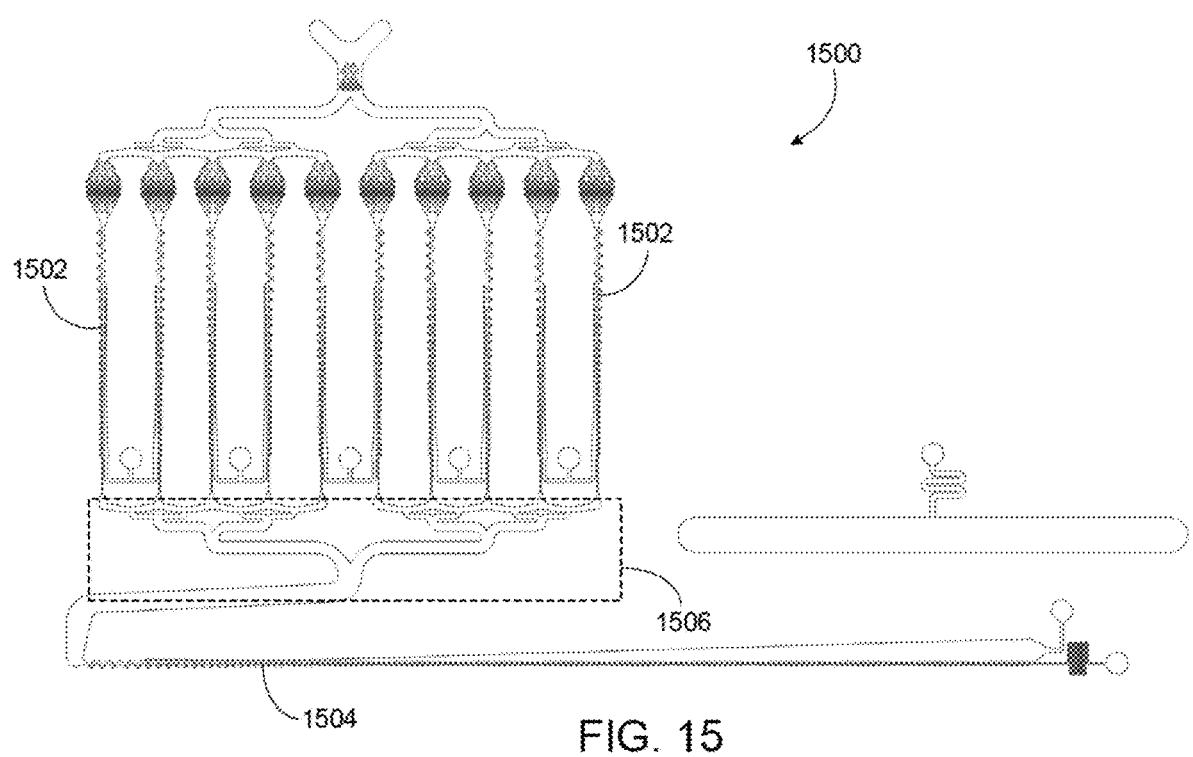
FIG. 15 is a schematic that illustrates a top view of a design of a microfluidic system.

Alternatively, or in addition, two or more devices may be constructed in series so that particle concentration/volume reduction is modified at each stage (i.e., device) of the overall system. To demonstrate the application of serial volume reduction, we constructed a microfluidic system containing serially integrated devices: in particular, we used ten parallel 10× devices that feed into a single 50× device for a theoretical overall volume reduction of 500×. FIG. 15 is a schematic that illustrates a top view of the design of the system 1500 used to study volume reduction, which includes ten parallel 10× concentrator devices 1502 and a single 50× concentrator device 1504. The operation of the system 1500 proceeds as follows: (i) dilute particles enter the system 1500 and are focused in the separate 10× concentrators 1502 into ten parallel focused streams; (ii) the ten parallel focused streams then are sent through a series of converging channels 1506; (iii) the converged streams then are refocused as they enter the 50× device 1504; and (iv) finally, all the particles exit through the bottom product outlet of the 50× device.

Due to the pressure requirements and PDMS deformation, the systems used for the experiments were fabricated in rigid epoxy in place of PDMS [Eugene J. Lim et al. "Inertio-elastic focusing of bioparticles in microchannels at high throughput," Nature Communications. 2014] (see, e.g., Martel, J. M. & Toner, M. "Particle Focusing in Curved Microfluidic Channels," Sci. Rep. 3, 1-8 (2013), incorporated herein by reference in its entirety). To test the yield, white blood cells at an input concentration of 100,000 per mL were introduced into the system. The yield of the integrated system was consistently above 95% and exhibited a volume reduction factor of ~411. Thus, for a 30 mL input sample containing 100,000 white blood cells per mL, the sample will be reduced by the microfluidic system into 73 μL+/−1.2 μL (n=5) with greater than 95% of the original cells (95.7%+/−3.6%, n=5). The discrepancy between the 411 volume reduction factor and 500 designed volume reduction factor is a difference of only a few microliters of product which was difficult to control as the input flow rate of 4 mL/min (pump driving force limitation) and the product flow rate of <10 μL/min. That is to say, that while the device was designed to perform 500× volume reduction, it actually performed 400× volume reduction. It is believed that the relative resistances of the product and waste channels were slightly off, such that slightly more volume went to the product than desired. Additionally, the tiny product volume may have caused some measurement error. Tiny fabrication imperfections in the microfluidic system can alter this balance as well.

Centrifugation used for washing cells, exchanging media and/or concentrating a sample for subsequent assays is one of the most widely utilized processes in the biomedical sciences. The system 1500 and the foregoing experimental results demonstrate that the microfluidic siphoning and inertial focusing devices are capable of accomplishing the foregoing common biomedical tasks typically performed with centrifugation in a continuous flow and sterile manner at throughputs of up to 4 mL/min (240 mL/hour) and at volume reduction factors of 20-fold or higher. Furthermore, the typical limitation on throughput of microfluidic devices is also mitigated using the combined siphoning and inertial focusing techniques. While we have presented a non-integrated single device which achieves a throughput of 500 µL/min at a volume reduction factor of 50×, the devices can be further arranged in parallel to obtain a set of greater than 40 channels (20 mL/min or 1200 mL/hr), diminishing the run time for the larger volume samples.

While much of the advancement presented is in terms of improving experimental methods there has also been a key finding about the nature of inertial focusing. The realization that the particle-free layer formation is not as sensitive to particle volume fraction as the single stream or high quality inertial focusing previously predicted may be intuitive, but also brings to light a new means of comparing inertial focusing device performance. There are typically five different geometries utilized in inertial focusing and typically are each compared by the length required to achieve a minimum streak width. By changing the definition of optimal focusing from minimizing streak width to the dynamic formation of the particle-free layer, new insights into the dynamics of focusing for different microfluidic structures can be investigated and directly compared. This new means of comparison could standardize how the effectiveness of this class of microfluidic devices is measured.

OTHER EMBODIMENTS

It is to be understood that while the invention has been described in conjunction with the detailed description thereof, the foregoing description is intended to illustrate and not limit the scope of the invention, which is defined by the scope of the appended claims.

What is claimed is:

1. A microfluidic device comprising:
a first module comprising a first microfluidic channel having a sample inlet at a first end of the first microfluidic channel, wherein the first microfluidic channel is configured to shift particles above a specific size to a first product outlet at a second end of the first microfluidic channel; and
a second module comprising:
an array of islands in a second microfluidic channel, a buffer inlet in fluid communication with a first end of the second microfluidic channel, and a product inlet in fluid communication with a first product outlet and a first end of the second microfluidic channel, wherein:
the array of islands is arranged in one or more rows that extend along a longitudinal direction in a corresponding microfluidic channel,
each island in a row is spaced apart from an adjacent island in the row to form a siphoning channel, and
the array of islands is configured and arranged to shift portions of fluid through the siphoning channel between adjacent islands within a row to a waste outlet, and to shift particles above a specific size into a buffer flowing in the second microfluidic channel and to a second product outlet;
wherein the first module and the second module are serially arranged such that a sample fluid having particles above the specific size flows from the first module to the second module.

2. The microfluidic device of claim 1, further comprising:
a third module comprising a set of microfluidic channels that are each configured to shift particles above the specific size to first product outlets at respective second ends of the set of microfluidic channels.

3. The microfluidic device of claim 1, wherein:
the first module comprises:
a first array of islands in the first microfluidic channel, wherein:
the first array of islands is arranged in one or more rows that extend along a longitudinal direction in the first microfluidic channel,
each island in a row is spaced apart from an adjacent island in the row to form a siphoning channel, and
the first array of islands is configured and arranged to shift portions of fluid through the siphoning channel between adjacent islands within a row to a waste outlet at a second end of the first microfluidic channel, and to shift particles above a specific size to a first product outlet at the second end of the first microfluidic channel; and
the second module comprises:
multiple arrays of islands in a corresponding microfluidic channel included in a set of microfluidic channels, each array of islands having a sample inlet at a first end of the corresponding microfluidic channel, wherein:
each array included in the multiple arrays of islands is arranged in one or more rows that extend along a longitudinal direction in a corresponding microfluidic channel,
each island in a row is spaced apart from an adjacent island in the row to form a siphoning channel, and
each array included in the multiple arrays of islands is configured and arranged to shift portions of fluid through the siphoning channel between adjacent islands within a row to a waste outlet at a second end of the corresponding microfluidic channel, and to shift particles above a specific size to first product outlets at the second end of the corresponding microfluidic channel.

4. The microfluidic device of claim 3, wherein the multiple arrays of islands include four arrays of islands arranged in parallel such that a different portion of the sample fluid introduced into the microfluidic device flows through each of the four arrays of islands.

5. The microfluidic device of claim 1, wherein each island included in the array of islands has a width between 150 and 250 micrometers, a length between 200 and 800 micrometers, and a height between 100 and 200 micrometers.

6. The microfluidic device of claim 1, wherein each island included in the array of islands has a length-to-width ratio greater than 1.25.

7. A microfluidic device comprising:
a first particle enrichment module comprising a first microfluidic channel having a sample inlet at a first end of the first microfluidic channel, wherein the first microfluidic channel is configured to shift particles above a specific size to a first product outlet at a second end of the first microfluidic channel; and
a particle separation module comprising:
an array of islands in a second microfluidic channel, a buffer inlet in fluid communication with a first end of the second microfluidic channel, and a product inlet in fluid communication with the first product outlet and a first end of the second microfluidic channel, wherein:
the array of islands is arranged in one or more rows that extend along a longitudinal direction in a corresponding microfluidic channel, each island in a row is spaced apart from an adjacent island in the row to form a siphoning channel, and the array of islands is configured and arranged to shift portions of fluid through the siphoning channel between adjacent islands within a row to a waste outlet, and to shift particles above a specific size into a buffer flowing in the second microfluidic channel and to a second product outlet;

wherein the first particle enrichment module and the particle separation module are serially arranged such that a sample fluid having particles above the specific size flows from the first particle enrichment module to the particle separation module.

8. The microfluidic device of claim 7, further comprising:

a second particle enrichment module comprising a set of microfluidic channels that are each configured to shift particles above the specific size to first product outlets at respective second ends of the set of microfluidic channels.

9. The microfluidic device of claim 8, wherein:

the first particle enrichment module comprises:

a first array of islands in the first microfluidic channel, wherein:

the first array of islands is arranged in one or more rows that extend along a longitudinal direction in the first microfluidic channel, each island in a row is spaced apart from an adjacent island in the row to form a siphoning channel, and the first array of islands is configured and arranged to shift portions of fluid through the siphoning channel between adjacent islands within a row to a waste outlet at a second end of the first microfluidic channel, and to shift particles above a specific size to a first product outlet at the second end of the first microfluidic channel; and the second particle enrichment module comprises:

multiple arrays of islands in a corresponding microfluidic channel included in the set of microfluidic channels, each array of islands having a sample inlet at a first end of the corresponding microfluidic channel, wherein:

each array included in the multiple arrays of islands is arranged in one or more rows that extend along a longitudinal direction in a corresponding microfluidic channel, each island in a row is spaced apart from an adjacent island in the row to form a siphoning channel, and each array included in the multiple arrays of islands is configured and arranged to shift portions of fluid through the siphoning channel between adjacent islands within a row to a waste outlet at a second end of the corresponding microfluidic channel, and to shift particles above a specific size to first product outlets at the second end of the corresponding microfluidic channel.

10. The microfluidic device of claim 9, wherein the multiple arrays of islands include four arrays of islands arranged in parallel such that a different portion of the sample fluid introduced into the microfluidic device flows through each of the four arrays of islands.

11. The microfluidic device of claim 7, wherein each island included in the array of islands has a width between 150 and 250 micrometers, a length between 200 and 800 micrometers, and a height between 100 and 200 micrometers.

12. The microfluidic device of claim 7, wherein each island included in the array of islands has a length-to-width ratio greater than 1.25.

13. A method comprising:

providing a sample fluid to a first module of a microfluidic device, wherein:

the first module comprises a first microfluidic channel having a sample inlet at a first end of the first microfluidic channel, wherein the first microfluidic channel is configured to shift particles above a specific size to a first product outlet at a second end of the first microfluidic channel, and the sample fluid is provided to the first module under conditions such that particle-free portions of the sample fluid are shifted through a siphoning channel between adjacent islands in a row, and an inertial lift force causes the particles above the specific size in the sample fluid to cross streamlines and transfer into a first portion of the sample fluid;

providing a buffer fluid to a second module of the microfluidic device, wherein:

the second module comprises:

a second array of islands in a second microfluidic channel, a buffer inlet in fluid communication with a first end of the second microfluidic channel, and a product inlet in fluid communication with the first product outlet and the first end of the second microfluidic channel, wherein:

the second array of islands is arranged in one or more rows that extend along a longitudinal direction a corresponding microfluidic channel, each island in a row is spaced apart from an adjacent island in the row to form a siphoning channel, and the second array of islands is configured and arranged to shift portions of fluid through the siphoning channel between adjacent islands within a row to a waste outlet, and to shift particles above a specific size into a buffer flowing in the second microfluidic channel and to a second product outlet; and passing, from the first module, the first portion of the sample fluid containing the transferred particles, to the second module, wherein the first portion of the sample fluid and the buffer fluid are each provided to the second module under conditions such that particle-free portions of the first portion of the sample fluid and the buffer fluid are shifted through the siphoning channel between adjacent islands in a row, an inertial lift force causes the particles in the sample fluid to cross streamlines and transfer into a collection channel of the microfluidic device.

14. A method of concentrating and extracting particles from a sample fluid, the method comprising:

providing the sample fluid to a first particle enrichment module of a microfluidic device, wherein:

the first particle enrichment module comprises a first microfluidic channel having a sample inlet at a first end of the first microfluidic channel, wherein the first microfluidic channel is configured to shift particles above a specific size to a first product outlet at a second end of the first microfluidic channel, and the sample fluid is provided to the first particle enrichment module under conditions such that particle-free portions of the sample fluid are shifted through a siphoning channel between adjacent islands in a row, and an inertial lift force causes the particles above the specific size in the sample fluid to cross streamlines and transfer into a first portion of the sample fluid;

providing a buffer fluid to a particle separation module of the microfluidic device, wherein:

the particle separation module comprises:

a second array of islands in a second microfluidic channel, a buffer inlet in fluid communication with a first end of the second microfluidic channel, and a product inlet in fluid communication with the first product outlet and the first end of the second microfluidic channel, wherein:

the second array of islands is arranged in one or more rows that extend along a longitudinal direction a corresponding microfluidic channel, each island in a row is spaced apart from an adjacent island in the row to form a siphoning channel, and the second array of islands is configured and arranged to shift portions of fluid through the siphoning channel between adjacent islands within a row to a waste outlet, and to shift particles above a specific size into a buffer flowing in the second microfluidic channel and to a second product outlet; and passing, from the first particle enrichment module, the first portion of the sample fluid containing the transferred particles, to the particle separation module, wherein the first portion of the sample fluid and the buffer fluid are each provided to the particle separation module under conditions such that particle-free portions of the first portion of the sample fluid and the buffer fluid are shifted through the siphoning channel between adjacent islands in a row, an inertial lift force causes the particles in the sample fluid to cross streamlines and transfer into a collection channel of the microfluidic device.

15. A method comprising:

providing a sample fluid to a first particle enrichment module of a microfluidic device, wherein:

the module comprises a microfluidic channel having a sample inlet at a first end of the microfluidic channel, wherein the microfluidic channel is configured to shift particles above a specific size to a product outlet at a second end of the microfluidic channel, and the sample fluid is provided to the module under conditions such that particle-free portions of the sample fluid are shifted through a siphoning channel between adjacent islands in a row, and an inertial lift force causes the particles above the specific size in the sample fluid to cross streamlines and transfer into a first portion of the sample fluid; and passing, from the first particle enrichment module, the first portion of the sample fluid containing the transferred particles, to a second module, wherein the first portion of the sample fluid and a buffer fluid are each provided to the second module under conditions such that particle-free portions of the first portion of the sample fluid and the buffer fluid are shifted through the siphoning channel between adjacent islands in a row, an inertial lift force causes the particles in the sample fluid to cross streamlines and transfer into a collection channel of the microfluidic device.

16. The method of claim 15, wherein the second module comprises a second array of islands in a second microfluidic channel, a buffer inlet in fluid communication with a first end of the second microfluidic channel, and a product inlet in fluid communication with the product outlet and the first end of the second microfluidic channel.

17. The method of claim 16, wherein the second array of islands is arranged in one or more rows that extend along a longitudinal direction a corresponding microfluidic channel.

18. The method of claim 16, wherein each island in a row is spaced apart from an adjacent island in the row to form a siphoning channel.

19. The method of claim 16, wherein the second array of islands is configured and arranged to shift portions of fluid through the siphoning channel between adjacent islands within a row to a waste outlet, and to shift particles above a specific size into a buffer flowing in the second microfluidic channel and to a second product outlet.

20. The method of claim 13, wherein the particles in the sample fluid comprises eggs.

21. The method of claim 13, wherein the particles in the sample fluid comprises sperm.

22. The method of claim 14, wherein the particles in the sample fluid comprises eggs.

23. The method of claim 14, wherein the particles in the sample fluid comprises sperm.

24. The method of claim 15, wherein the particles in the sample fluid comprises eggs.

25. The method of claim 15, wherein the particles in the sample fluid comprises sperm.

* * * * *

UNITED STATES PATENT AND TRADEMARK OFFICE
CERTIFICATE OF CORRECTION

| | | |
|---|---|---|
| PATENT NO. | : 12,220,704 B2 | Page 1 of 1 |
| APPLICATION NO. | : 18/595927 | |
| DATED | : February 11, 2025 | |
| INVENTOR(S) | : Ravi Kapur, Kyle C. Smith and Mehmet Toner | |

It is certified that error appears in the above-identified patent and that said Letters Patent is hereby corrected as shown below:

In the Claims

Column 48, Line 31:
In Claim 13, delete "a" and insert -- in a --

Column 49, Line 15:
In Claim 14, delete "a" and insert -- in a --

Column 50, Line 25 (Approx.):
In Claim 17, delete "a" and insert -- in a --

Signed and Sealed this
Seventh Day of October, 2025

John A. Squires
*Director of the United States Patent and Trademark Office*